(12) United States Patent
Griffin et al.

(10) Patent No.: US 7,718,168 B2
(45) Date of Patent: May 18, 2010

(54) MEDICAL IMPLANT MATERIALS CONTAINING IMMOBILIZED TRANSGLUTAMINASE

(75) Inventors: Martin Griffin, Nottingham (GB); Deborah J. Heath, York (GB); Paul Christian, Derbyshire (GB)

(73) Assignee: Aston University, Birmingham (GB)

( * ) Notice: Subject to any disclaimer, the term of this patent is extended or adjusted under 35 U.S.C. 154(b) by 1017 days.

(21) Appl. No.: 10/276,230

(22) PCT Filed: May 2, 2001

(86) PCT No.: PCT/GB01/01910

§ 371 (c)(1),
(2), (4) Date: Jul. 9, 2003

(87) PCT Pub. No.: WO01/85224

PCT Pub. Date: Nov. 15, 2001

(65) Prior Publication Data

US 2004/0030408 A1    Feb. 12, 2004

(30) Foreign Application Priority Data

May 12, 2000    (GB) .................................. 0011356.3

(51) Int. Cl.
*A61K 38/43* (2006.01)
*A61F 2/00* (2006.01)
*C12N 11/02* (2006.01)
*C12N 11/08* (2006.01)
*C12N 9/99* (2006.01)

(52) U.S. Cl. .................. 424/94.1; 424/423; 435/177; 435/180; 435/183

(58) Field of Classification Search .................. None
See application file for complete search history.

(56) References Cited

U.S. PATENT DOCUMENTS

| 5,939,385 | A | 8/1999 | Labroo et al. .................. 514/12 |
| 6,919,076 | B1 * | 7/2005 | Green et al. ............... 424/94.5 |

FOREIGN PATENT DOCUMENTS

| EP | 0 530 804 A1 | 3/1993 |
| EP | 0 856 355 A2 | 8/1998 |
| JP | 02 086743 A | 3/1990 |
| WO | WO 94/28949 | 12/1994 |
| WO | WO 97/40701 | 11/1997 |
| WO | WO 98/43686 | 10/1998 |

OTHER PUBLICATIONS

Heath. D.J. et al. (2000). "Human Osteoblast Response to Tissue Transglutaminase Precoated Poly(ε-Caprolactone)," Abstract, *Transactions of the Sixth World Biomaterials Congress*, vol. 1, May 15-20, 2000, Hawaii, USA, Abstract 351.
Achyuthan, et al. "Identification of a Guanosine Triphosphate-binding Site on Guinea Pig Liver Transglutaminase," Journal of Biological Chemistry 262(4):1901-1906 (Feb. 5, 1987).
Achyuthan et al., "Immunochemical analyses of human plasma fibronectin-cytosolic transglutaminase interactions," Journal of Immunological Methods 180:69-79 (1995).
Aeschlimann et al., "Expression of Tissue Transglutaminase in Skeletal Tissues Correlates with Events of Terminal Differentiation of Chondrocytes," The Journal of Cell Biology 120(6):1461-1470 (Mar. 1993).
Aeschlimann et al., "Transglutaminases: Protein Cross-Linking Enzymes in Tissues and Body Fluids," Thrombosis and Haemostasis 71(4):402-415 (1994).
Aeschlimann et al., "Transglutaminase-catalyzed Matrix cros-linking in Differentiating Cartilage: Identification of Osteonectin as a Major Glutaminyl Substrate," The Journal of Cell Biology 129(3):881-892 (May 1995).
Aeschlimann et al., "Tissue Transglutaminase and Factor XIII in Cartilage and Bone Remodeling," Seminars in Thrombosis and Meostasis 22(5):437-443 (1996).
Akimov, "Tissue Transglutaminase Is an Integrin-binding Adhesion Coreceptor for Fibronectin," Journal of Cell Biology 148(4):825-838 (Feb. 21, 2000).

(Continued)

*Primary Examiner*—David M Naff
(74) *Attorney, Agent, or Firm*—Morrison & Foerster LLP

(57) ABSTRACT

The present invention provides a medical implant material comprising mammalian transglutaminase and a polymer, wherein the transglutaminase is provided in the absence of free divalent metal ions and wherein the polymer is associated with the transglutaminase binding protein. Preferably, the transglutaminase is a tissue transglutaminase, which is coated on, impregnated into or covalently linked to the polymer. The polymer may be naturally occuring or synthetic, and may be biodegradable or non-biodegradable. The medical implant material may further comprise a reinforcing agent and/or one or more additional polymers. The invention further provides the use of a mammalian transglutaminase in a method for improving the biocompatibility of a medical implant material, the method comprising the steps of (i) providing a medical implant material comprising a polymer associated with a binding protein for binding the transglutaminase, and (ii) treating said material with a mammalian transglutaminase.

37 Claims, 25 Drawing Sheets

OTHER PUBLICATIONS

Ali et al., "In vitro Hydroxyl Radical Degradation of Polycaprolactone," Biomaterial-Tissue Interfaces 10:399-403 (1992).

Ali et al., "Mechanisms of polymer degradation in implantable devices," Biomaterials 14(9):648-656 (1993).

Ali et al., "Molecular biointeractions of biomedical polymers with extracellular exudates and inflammatory cells and their effects on the biocompatibility, in vivo," Biomaterials 15(10):779-785 (1994).

Barsigian et al., "Tissue (Type II) Transglutaminase Covalently Incorporates Itself, Fibrinogen, or Fibronectin into High Molecular Weight Complexes on the Extracellular Surface of Isolated Hepatocytes," The Journal of Biological Chemistry 266(33):22501-22509 (1991).

Bei et al., "Polycaprolatone-poly (Ethylene Glycol) Block Copolymer III Drug Release Behavior," Chinese Journal of Polymer Science 13(2):154-161 (1995).

Bendixen et al., "Transglutaminases Catalyze Cross-linking of Plasminogen to Fibronectin and Human Endothelial Cells," The Journal of Biological Chemistry, 268(29):21962-21967 (Oct. 15, 1993).

Beninati et al., "Osteopontin: Its Transglutaminase-Catalyzed Post-translational Modifications and Cross-Linking to Fibronectin," J. Biochem. 115(4):675-682 (1994).

Blitterswijk et al., "Reactions of cells at implant surfaces," Biomaterials 12:187-193 (Mar. 1991).

Borge et al., "Type II transglutaminase expression in rabbit articular chondrocytes in culture: relation with cell differentiation, cell growth, cell adhesion and cell apoptosis," Biochimica et Biophysica Acta 1312:117-124 (1996).

Bowness et al., "Increased transglutaminase activity during skin wound healing in rats," Biochmica et Biophysica Acta 967:234-240 (1988).

Casadio et al., "The structural basis for the regulation of tissue transglutaminase by calcium ions," Eur. J. Biochem. 262:672-679 (1999).

Cascone et al., "Collagen and hyaluronic acid based polymeric blends as drug delivery systems for the release of physiological concentrations of growth hormone," Journal of Materials Science: Materials in Medicine 5:770-774 (1994).

Cha et al., "The biodegradability of polyester blends," Biomaterials 11:108-113 (1990).

Clark et al., "Integrins and Signal Transduction Pathways: The Road Taken," Science 268:233-239 (Apr. 14, 1995).

Coombes et al., "Resorbable Synthetic Polymers as Replacements for Bone Graft," Clinical Materials 17:35-67 (1994).

Daniels et al., "Mechanical Properties of Biodegradable Polymers and Composites Proposed for Internal Fixation of Bone," Journal of Applied Biomaterials 1:57-78 (1990).

Demignot et al., "Transglutaminase activity in rabbit articular chondrocytes in culture," Biochimica et Biophysica Acta 1266:163-170 (1995).

Dzamba et al., "Substrate-specific Binding of the Amino Terminus of Fibronectin to an Integrin Complex in Focal Adhesions," The Journal of Biological Chemistry 269(30):19646-19652 (Jul. 29, 1994).

Ellis et al., "Recent advances in tissue synthesis in vivo by use of collagen—glycosaminoglycan copolymers," Biomaterials 17(3):291-299 (1996).

Feng et al., "Syntehsis and Evaluation of Biodegradable Block Copolymers of $\epsilon$—Caprolactone and $_{DL}$-Lactide," Journal O Fpolymer Science: Polymer Letters Edition 21:593-600 (1983).

Fesus et al., "Transglutaminase-sensitive glutamine residues of human plasma fibronectin revealed by studying its proteolytic fragments," J. Biochem. 154:371-374 (1986).

Fraij et al., "Organization and tracture of the human tissue transglutaminase gene," Biochimica et Biophysica Acta 1345:65-71 (1997).

Gaudry, "Tissue Transglutaminase: A New Secretory Protein," PhD Thesis, The Nottingham Trent University p. 48 (May 1998).

Gaudry et al., "Tissue Transglutaminase is an Important Player at the Surface of Human Endothelial Cells: Evidence for its Externalization and its Colocalization with the $\beta_1$ Integrin," Experimental Cell Research 252:104-113 (1999).

Gentile et al., "Expression of Tissue Transglutaminase in Balb-C 3T3 Fibroblasts: Effects on Cellular Morphology and Adhesion," The Journal of Cell Biology 119(2):463-474 (Oct. 1992).

Gentile et al., "Isolation and Characterization of cDNA Clones to Mouse Macrophage and Human Endothelial Cell Tissue Transglutaminases," The Journal of Biological Chemistry 266(1):478-483 (Jan. 5, 1991).

Griffin et al., "Transglutaminases: Nature's biological glues," Biochem. J. 368:377-396 (2002).

Grootjans et al., "Substrate Requirements for Transglutaminases," The Journal of Biological Chemistry 270(39):22855-22858 (Sep. 29, 1995).

Giusti et al., "Collagen-based new bioartificial polymeric materials," Biomaterials 15(15):1229-1233, (1994).

Greenberg et al., "Transglutaminases: multifunctional cross-linking enzymes that stabilize tissues," The FASEB Journal 5:3071-3077 (Dec. 1991).

Groenen et al., "The amin-donor substrate specificity of tissue-type transglutaminase Influence of amino acid residues flanking the amine-donor lysine residue," Eur. J. Biochem. 220:795-799 (1994).

Grundmann et al., "Characterization of cDNA coding for human factor XIIIa," Proc. Natl. Acad. Sci. USA 83:8024-8028 (Nov. 1986).

Gurav et al., "A qualitative in vitro evaluation of the degradable materials poly(caprolactone), poly(hydroxybutyrate) and a poly (hydroxybutyrate)-(hydroxyvalerate) copolymer," Journal of Materials Science: Materials in Medicine 5:784-787 (1994).

Gurav et al., "In-Vitro Biocompatibility Testing of Degradable Polymers," Fifth World Biomaterials Congress, Toronto, Canada p. 63 (May 29-Jun. 2, 1996).

Heath et al., "Characterization of Tissue Transglutaminase in Human Osteoblast-like Cells," Journal of Bone and Mineral Research 16(8):1477-1485 (2001).

Heath et al., "Involvement of tissue transglutaminase in the stabilization of biomaterial/tissue interfaces important in medical devices," Biomaterials 23:1519-1526 (2002).

Heath, "The Stabilisation of the Extracellular Matrix of Bone on Biomaterial Surfaces," Thesis, University of Nottingham (Aug. 2000).

Hohenadl et al., "Two Adjacent N-terminal Glutamines of BM-40 (Osteonectin, SPARC) Act as Amine Acceptor Sites in Transglutaminase $_c$-catalyzed Modification," The Journal of Biological Chemistry 270(40):23415-23420 (Oct. 6, 1995).

Jeong et al., "The Fibronectin-binding Domain of Transglutaminase," The Journal of Biological Chemistry 270(10):5654-5658 (Mar. 10, 1995).

Jones et al., "Reduced expression of tissue transglutaminase in a human endothelial cell line leads to changes in cell spreading, cell adhesion and reduced polymerization of fibronectin," Journal of Cell Science 110:2641-2472 (1997).

Juliano et al., "Signal Transduction from the Extracellular Matrix," The Journal of Cell Biology 120(3):577-585 (Feb. 1993).

Jürgensen et al., "A New Biological Glue for Cartilage-Cartilage Interfaces: Tissue Transglutaminase," The Journal of Bone and Joint Surgery 79-A(2):185-193 (Feb. 1997).

Kaartinen et al., "Transglutaminase-catalyzed Cross-linking of Osteopontin Is Inhibited by Osteocalcin," The Journal of Biological Chemistry 272(36):22736-22741 (Sep. 5, 1997).

Kaartinen et al., "Cross-linking of Osteopontin by Tissue Transglutaminase Increases Its Collagen Binding Properties," The Journal of Biological Chemistry 274(3):1729-1735 (Jan. 15, 1999).

Lemmouchi et al., "Biodegradable polyesters for controlled release of trypanocidal drugs: In vitro and in vivo studies," Biomaterials 19:1827-1837 (1998).

LeMosy et al., "Visualization of Purified Fibronectin-Transglutaminase Complexes," The Journal of Biological Chemistry 267(11):7880-7885 (Apr. 15, 1992).

Lesort et al., "Distinct Nuclear Localization and Activity of Tissue Transglutaminase," The Journal of Biological Chemistry 273(20):11991-11994 (May 15, 1998).

Lowry et al., "Polycaprolactone/glass bioabsorbable implant in a rabbit humerus fracture model," Journal of Biomedical Materials Research 36:536-541 (1997).

Nicolas, "A study of extracellular and intracellular tissue transglutaminase activity," PhD Thesis, The Nottingham Trent University (1998).

Peluso et al., "Cell-biomaterial interactions: role of transglutaminase enzyme," Journal of Materials Science: Materials in Medicine 7:707-711(1996).

Pitt et al., "Aliphatic Polyesters. I. The Degradation of Poly(ε-caprolactone) In Vivo," Journal of Applied Polymer Science 26:3779-3787 (1981).

Pitt et al., "Modification of the Rates of Chain Cleavage of Poly (ε-caprolactone) and Related Polyesters in the Solid State," Journal of Controlled Release 4:283-292 (1987).

Pitt et al., "Sustained Drug Delivery Systems. I. The Permeability of Poly(ε-caprolactone), Poly(DL-Lactic Acid), and Their Copolymers," Journal of Biomedical Materials Research 13:497-507 (1979).

Quade et al., "Fibronectin's Amino-terminal Matrix Assembly Site Is Located within the 29-kDa Amino-terminal Domain Containing Five Type I Repeats," The Journal of Biological Chemistry 263(36):19602-19609 (Dec. 25, 1988).

Rago et al., "DNA Fluorometric Assay in 96-Well Tissue Culture Plates Using Hoechst 33258 after Cell Lysis by Freezing in Distilled Water," Analytical Biochemistry 191:31-34 (1990).

Ruoslahti et al., "Extracellular Matrices and Cell Adhesion," Arteriosclerosis 5:581-594 (Nov./Dec. 1985).

Schamberger et al., "Surface chemical modifications of materials which influence animal cell adhesion—a review," Colloids and Surfaces B: Biointerfaces 2:209-223 (1994).

Schwartz et al., "A 50-kDa Integrin-associated Protein Is Required for Integrin-regulated Calcium Entry in Endothelial Cells," The Journal of Biological Chemistry 268(27):19931-19934 (Sep. 25, 1993).

Sinha et al., "Surface Composition of Orthopaedic Implant Metals Regulates Cell Attachment, Spreading, and Cytoskeletal Organization of Primary Human Osteoblasts In Vitro," Clinical Orthopaedics and Related Research 305:258-272 (1994).

Smethurst et al., "Measurement of tissue transglutaminase activity in a permeabilized cell system: its regulation by $Ca^{2+}$ and nucleotides," Biochem. J. 313:803-808 (1996).

Smith et al., "Bioerodible polymers for delivery of macromolecules," Advanced Drug Delivery Reviews 4:343-357 (1990).

Taylor et al., "Six Bioabsorbable Polymers: In Vitro Acute Toxicity of Accumulated Degradation Products," Journal of Applied Biomaterials 5:151-157 (1994).

Ueki et al., "Dual functions of transglutaminase in novel cell adhesion," Journal of Cell Science 109:2727-2735 (1996).

Upchurch et al., "Localization of Cellular Transglutaminase on the Extracellular Matrix After Wounding: Characteristics of the Matrix Bound Enzyme," Journal of Cellular Physiology 149:375-382 (1991).

Verderio et al., "Regulated Expression of Tissue Transglutaminase in Swiss 3T3 Fibroblasts: Effects on the Processing of Fibronectin, Cell Attachment, and Cell Death," Experimental Cell Research 239:119-138 (1998).

Verderio et al., "Role of the cross-linking enzyme tissue transglutaminase in the biological recognition of synthetic biodegradable polymers," J. Biomed. Mater. Res. 54:294-304 (2000).

Vert et al., "Bioresorbability and biocompatibility of aliphatic polyesters," Journal of Materials Science: Materials in Medicine 3:432-446 (1992).

* cited by examiner

MEDICAL IMPLANT MATERIALS CONTAINING IMMOBILIZED TRANSGLUTAMINASE

CROSS-REFERENCE TO RELATED APPLICATIONS

This application is a National Phase application under 35 U.S.C. § 371 of International Application No. PCT/GB01/01910 filed May 2, 2001 and claims the benefit of Great Britain Application No. 0011356.3 filed May 12, 2000.

The present invention relates to materials for use in medicine, in particular medical implant materials. The invention further provides a method of improving the biocompatibility of a medical implant material.

BACKGROUND

The use of artificial biomaterials is becoming increasingly widespread in several areas of medical treatment. For example, biomaterials are now used in the repair of damaged tissue (e.g. bone and skin), in prosthetic devices such as artificial hip and knee joints, heart valves, and blood vessels, and in drug delivery devices. However, one of the challenges that remains in this field of medicine is the provision of biomaterials with improved biocompatibility properties, which can be readily colonized by host cells.

The study of implant surface and biomaterial tissue interface reactions is essential for the continued improvement of implant performance. A review by Blitterwijk et al., (1991) discusses the importance of the reactions of cells at implant surfaces in determining the biocompatibility of the implant (i.e. how well the implant is accepted by the surrounding tissues and by the body as a whole). Current research is aimed at making 'bioactive materials' that will readily permit integration of the material into the host tissue.

There is considerable interest in poly($\epsilon$-caprolactone) (PCL) as a potential bioactive material. It has been widely used for the last thirty years for the production of resorbable sutures, biomedical implants, drug delivery systems and vaccine formulation. Currently, PCL is being exploited for bone graft substitution (Coombes and Meikle, 1994), because it could overcome the problems of limited supply of bone, risk of infection such as HIV, additional surgical operations and long bony union times associated with either autografts or allografts.

PCL is a semi-crystalline linear resorbable synthetic aliphatic polyester, —(—O—(CH$_2$)$_5$—CO—)—. When implanted in vivo, the polymer is readily degraded non-specifically by hydrolytic enzymes, esterases and carboxypeptidases. Pitt et al. (1981), showed that degradation of PCL in vivo and in vitro proceeds via hydrolytic chain scission of ester linkages until the segments are sufficiently small to diffuse through the polymer bulk. Once the polymer reaches the molecular weight of 5000 Daltons, significant weight loss is observed, which is dependent on particle size. Chain scission has also been shown to be associated with an increase in crystallinity, which partially determines the rate of degradation (see review by Smith et al., 1990).

The products generated from the degradation of PCL are either incorporated into the tricarboxylic acid (TCA) cycle and removed by the lungs in the form of carbon dioxide and water, or eliminated by direct renal secretion. Taylor et al. (1994) tested PCL in vitro for the acute toxicity of degradation products. They found that the pH of PCL in sterile distilled water and Tris buffer remained relatively constant over sixteen weeks, and that the samples degraded slightly more in Tris compared to in water. It has also been found that hydroxy radicals produced by inflammatory cells play a major role in the degradation of PCL in vitro (Ali et al., 1992, 1993) and in vivo (Ali et al., 1994). The bioresorbability and biocompatibility of PCL is reviewed by Vert et al., (1992).

Another favourable factor of PCL is that it can be blended with numerous other polymers, e.g. Poly(L-Lactide) (PLA), to produce co-polymers with optimised properties. PLA is one of the strongest polyesters and has a resorption time of greater than one year, probably in the range of 2-3 years. This would be advantageous, for example, in a 3-D tissue construct/scaffold, where the implant resorption rate needs to be adjusted according to the tissue repair rate.

Feng et al., (1983) synthesised a biodegradable block copolymer of poly($\epsilon$-caprolactone) with poly(DL-lactide). The copolymers possessed release properties similar to silicone rubber (one of the first non-degradable drug delivery systems) but their degradation rates were always faster than that of PCL or PLA homopolymers. They intended to combine the excellent permeability of PCL with the faster biodegradation rate of PLA. Pitt et al., (1979) did investigate PCL, PLA and their copolymers and demonstrated how variabilities in the permeability of the drug delivery system could be achieved using copolymers of PCL and PLA, because PCL is more permeable than PLA.

Jianzhong et al, 1995 used PCL and poly(ethylene glycol) (PEG) block copolymers as a drug release device. It was found that the increasing PEG content of the copolymer caused an increase in the hydrophilicity and a decrease in the crystallinity of the copolymer. Thus, the drug releas behaviour and the degradability of the copolymer can be controlled by adjusting the composition of the copolymer.

Chan and Pitt (1990) tested the degradability of PCL when fabricated by compression moulding, co-precipitation and solvent evaporation and found that the method of fabrication and the resulting morphology of the polymers plays a critical role in determining their relative rates of hydrolytic degradation. Compression moulding of PCL/polyglycolic acid-co-lactic acid blends, increased the rate of chain scission as compared to the other fabrication methods.

A problem with PCL is that it is a plastic at body temperature. Its mechanical properties make it ideal for drug delivery systems, but not for the internal fixation of bone. Lowry et al., (1997) made reinforced PCL with phosphate glass fibres in the form of intra-medullary pins for the internal fixation of bone. This study was performed in the rabbit model and histological evidence showed that the composite was well tolerated, with minimal inflammation around the pin. The review by Daniels et al. (1990) illustrates that the mechanical properties of polymers and composites can be improved by reinforcing the materials with alumina, alumina-boria-silica, calcium metaphosphate glass fibers and carbon.

As well as blending PCL with other synthetic polymers to control the degradation rate, improve the mechanical properties of the system and alter its permeability, PCL can also be blended with natural polymers, e.g. collagen, fibronectin, hyaluronic acid and glycosaminoglycans. These natural polymers are all part of the extracellular matrix (ECM) that cells produce and secrete. It is thought that by incorporating natural polymers with synthetic polymers, osteoconductance and biocompatibility properties could be combined with the physical and mechanical properties of the synthetic component, making bioartificial polymers a good bioactive biomaterial substitute.

Giusti et al., (1994) discuss the importance of blending collagen with polymeric materials for use as medical devices and show how blending also increases the mechanical and thermal properties as compared to the individual components. Cascone et al., (1994) demonstrated the use of collagen and hyaluronic acid based polymeric bioartificial polymers as a successful drug delivery system for the release of growth hormone.

Several reports have shown the importance of the ECM in cellular function Ruoslahti et al., 1985 and Ellis and Yannis, 1996). Cells initially attach to the biomaterial by physicochemical factors, e.g. charge, surface free energy or the water content of the biomaterial (Schamberger and Gardella, 1994), and then strongly adhere to ECM proteins, which have been deposited on the biomaterial surface. How the ECM is deposited, stabilised and configured on a particular biomaterial surface is still not known, however tissue transglutaminase (tTG) has been implicated in the stabilisation process. It is important to understand this process in order to control cellular responses to surfaces.

Transglutaminases (Enzyme Commission System of Classification 2.3.2.13) are a group of multifunctional enzymes that cross-link and stabilise proteins in tissues and body fluids (Aeschlimann and Paulsson, 1994 and Greenberg et al., 1991). In mammals, they are calcium dependent and catalyse the post-translational modification of proteins by forming inter and intra-molecular ε(γ-glutamyl) lysine cross-links. The bonds that form are stable, covalent and resistant to proteolysis, thereby increasing the resistance of tissues to chemical, enzymatic and physical disruption. In contrast to transglutaminases of mammalian origin, microbial transglutaminases are generally not $Ca^{2+}$-dependent.

The number of proteins acting as glutaminyl substrates for transglutaminases is highly restricted since both the primary structure and conformation are critical. In contrast, the only requirement of the acyl-acceptor substrate is the presence of a suitable pi amine, e.g. the ε-amino group of peptide bound lysine residues and small primary amines. Different types of transglutaminase enzyme differ in their specificity for a given glutaminyl substrate. For example, the plasma transglutaminase blood coagulation factor XIIIa acts on a limited range of glutaminyl substrates compared to tissue (or type II) transglutaminase (tTG). Unlike Factor XIIIa, tTG also binds GTP and GDP, which is thought to be important in its regulation by $Ca^{2+}$ (see Smethurst and Griffin, 1996). A further key difference between the types of transglutaminase is in their distribution.

Although tTG has been mainly described as a cytosolic enzyme and does not contain a typical hydrophobic leader sequence for secretion, it may be found both in the cytosol and membrane associated depending on the cell type. The biological function of tTG has yet to be determined. However, there is now increasing evidence to suggest that tTG can act at the cell surface, facilitating cell adhesion (Borge et al., 1996) and cell spreading (Jones et al., 1997) and the modification of the extracellular matrix (ECM) (Aeschlimann et al., 1995, Barsigian et al., 1991, Bowness et al., 1988 and Bendixen et al., 1993).

The ability of transglutaminase enzymes to cross-link proteins has been exploited in the development of biological glues for promoting adhesion between tissue surfaces. For example, biological adhesive compositions comprising a tissue transglutaminase are disclosed in WO 94/28949. These compositions also comprise a divalent metal ion co-factor, which plays a regulatory role in the functional activity of transglutaminase enzymes (see Casadio et al., 1999, Eur. J. Biochem. 262, 672-679).

SUMMARY OF THE INVENTION

A first aspect of the invention provides a medical implant material comprising a mammalian transglutaminase and a polymer, wherein the transglutaminase is provided in the absence of free divalent metal ions and wherein the polymer is associated with a binding protein for binding the transglutaminase.

By 'medical implant material' we include a material for implantation into the human or animal body, such as a material for use as an artificial tissue (e.g. bone, teeth and skin), prosthetic devices (e.g. joints, heart valves, blood vessels) and drug delivery devices.

By 'mammalian transglutaminase' we mean a member of the group of enzymes identified by Enzyme Commission System of Classification No. 2.3.2.13 (EC 2.3.2.13), wherein the enzyme is derived, directly or indirectly, from a mammalian source. Thus, we include transglutaminase prepared (i.e. extracted) from mammalian tissue samples, as well as mammalian transglutaminases expressed by recombinant means. We also include variants of naturally-occurring mammalian transglutaminases.

By 'free divalent metal ions' we mean unchelated divalent metal ions, such as $Ca^{2+}$ ions, which are available to interact with the transglutaminase and regulate the functional activity of the enzyme.

By 'provided in the absence of' free divalent metal ions we include transglutaminases which are provided in the presence of divalent metal ions that are bound to a chelating agent, and hence are not available to interact with the enzyme.

In a preferred embodiment of the first aspect of the invention the transglutaminase is a tissue transglutaminase.

In an alternative embodiment the transglutaminase is a plasma transglutaminase.

Preferably, the transglutaminase is prepared from mammalian tissue or cells.

More preferably, the transglutaminase is prepared from human tissue or cells. For example, the transglutaminase may be extracted from human tissue sources such as lung, liver, spleen, kidney, heart muscle, skeletal muscle, eye lens, endothelial cells, erythrocytes, smooth muscle cells, bone and macrophages. Advantageously, the transglutaminase is a tissue transglutaminase derived from human red cells (erythrocytes), or a plasma transglutaminase derived from either human placenta or human plasma.

Alternatively, the transglutaminase may be obtained from a culture of human cells that express a mammalian transglutaminase, using cell culture methodology well known in the art. Preferred cell line sources of such transglutaminases include human endothelial cell line ECV304 (for tissue transglutaminase) and human osteosarcoma cell line MG63.

It will be appreciated by those skilled in the art that the source of the transglutaminase may be selected according to the particular use (e.g. site of implantation) of the medical implant material. For example, if the medical implant material is to be used as artificial bone, it may be beneficial for the material to comprise a bone-derived transglutaminase.

In an alternative embodiment of the first aspect of the invention, the transglutaminase is a recombinant transglutaminase. For example, recombinant factor XIII production is described in European Patent Application No. EP 268 772 A.

Nucleic acid molecules encoding a transglutaminase are known in the art. For example, the coding sequence for human coagulation factor XIII A1 polypeptide is disclosed in Grundmann et al, 1986, *Proc. Natl. Acad. Si. USA* 83(21), 8024-8028 (accession no. NM 000129). The coding sequence for human tissue transglutaminase is disclosed in Gentile et al., 1991, *J. Biol. Chem.* 266(1) 478-483 (accession no. M 55153).

Nucleic acid molecules encoding a transglutaminase may be used in accordance with known techniques, appropriately modified in view of the teachings contained herein, to construct an expression vector, which is then used to transform an appropriate host cell for the expression and production of the polypeptide of the invention. Methods of expressing proteins in recombinant cells lines are widely known in the art (see Sambrook et al. (1989) *Molecular Cloning, A Laboratory Manual*, Second Edition, Cold Spring Harbor, N.Y.). Exemplary techniques also include those disclosed in U.S. Pat. Nos. 4,440,859 issued Apr. 3, 1984 to Rutter et al, 4,530,901 issued Jul. 23, 1985 to Weissman, 4,582,800 issued Apr. 15, 1986 to Crowl, 4,677,063 issued Jun. 30, 1987 to Mark et al, 4,678,751 issued Jul. 7, 1987 to Goeddel, 4,704,362 issued Nov. 4, 1987 to Itakura et al, 4,710,463 issued Dec. 1, 1987 to Murray, 4,757,006 issued Jul. 12, 1988 to Toole, Jr. et al, 4,766,075 issued Aug. 23, 1988 to Goeddel et al and 4,810,648 issued Mar. 7, 1989 to Stalker, all of which are incorporated herein by reference.

The nucleic acid molecule, e.g. cDNA, encoding the transglutaminase may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading fame for expression If necessary, the DNA may be linked to the appropriate transcriptional and rational regulatory control nucleotide sequences recognised by the desired host, although such controls are generally available in the expression vector.

Thus, the DNA insert may be operatively linked to an appropriate promoter. Bacterial promoters include tile *E. coli* lacI and lacZ promoters, the T3 and T7 promoters, die gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. Alternatively, the Baculovirus expression system in insect cells may be used (see Richardson et al., 1995), *Methods in Molecular Biology* V$_o$l 39, J Walker ed., Humana Press, Totowa, N.J.). The expression constructs will desirably also contain sites for transcription initiation and termination, and in the transcribed region, a ribosome binding site for translation. (Hastings et al, International Patent No. WO 98/16643, published Apr. 23, 1998).

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the transglutaminase, which can then be recovered.

The recombinant transglutaminase can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Many expression systems are known, including systems employing: bacteria (e.g. *E. coli* and *Bacillus subtillis*) transformed with, for example, recombinant bacteriophage, plasmid or cosmid DNA expression vectors; yeasts (e.g. *Saccaromyces cerevisiae*) transformed with, for example, yeast expression vectors; insect cell systems transformed with, for example, viral expression vectors (e.g. baculovirus); plant cell systems transfected with, for example viral or bacterial expression vectors; animal cell systems transfected with, for example, adenovirus expression vectors.

The vectors include a prokaryotic replicon, such as the Col E1 ori, for propagation in a prokaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are: pUC18; pUC19, pBR322 and pBR329 available from Biorad Laboratories (Richmond, Calif., USA); pTc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. Examples of an inducible mammalian expression vectors include pMSG, also available from Pharmacia (Piscataway, N.J., USA), and the tetracycline (tet) regulatable system, available form Clontech. The pMSG vector uses the glucocorticoid-inducible promoter of the mouse mammary tumour virus long terminal repeat to drive expression of the cloned gene. The tet regulatable system uses the presence or absence of tetracycline to induce protein expression via the tet-controlled transcriptional activator.

Useful yeast plasmid vectors are pRS403-406 and pRS413-416 and are generally available from Stratagene Cloning Systems La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression, vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or E. coli DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzyme to create cohesive ends and ligated to an expression vector with compatible termini. Adaptors are also chemically synthesised DNA fragments which contain one blunt end used for ligation but which also possess one pre-formed cohesive end.

Synthetic linkers containing a variety of restriction endonuclease sites are commercially available from a member of sources including International Biotechnologies Inc, New Haven, Conn., USA.

A desirable way to modify the nucleic acid molecule encoding the transglutaminase is to use the polymerase chain reaction as disclosed by Saiki et al (1988) Science 239, 487-491. In this method the nucleic acid molecule, e.g. DNA, to be enzymatically amplified is flaked by two specific oligonucleotide primers which themselves become incorporated into the amplified DNA. The said specific primers may contain restriction endonuclease recognition sites which can be used for cloning into expression vectors using methods known in the art.

Conveniently, the mammalian transglutaminase is a variant transglutaminase.

By "a variant" we include a polypeptide comprising the amino acid sequence of a naturally occurring mammalian transglutaminase wherein there have been amino acid insertions, deletions or substitutions, either conservative or non-conservative, such that the changes do not substantially reduce the activity of the variant compared to the activity of the activated naturally occurring mammalian transglutaminase. For example, the variant may have increased activity compared to the activity of the naturally occurring transglutaminase.

Alternatively, the variant may have increased ability to facilitate the colonisation of medical implants by cells, wherein said increased ability is independent of the enzyme activity of the variant but is related to some other property of the variant. For example, increased ability of the variant transglutaminase to facilitate the colonisation of medical implants by cells may be associated with an increased ability to bind endogenous (i.e. host) proteins such as receptors.

The enzyme activity of variant mammalian transglutaminases may be measured by the biotin-cadaverine assay, as described in the Examples and as published in (Jones et al., 1997, J. Cell. Sci. 110, 2461-2472). For example, reduced expression of tissue transglutaminase in a human endothelial cell line leads to changes in cell spreading, cell adhesion and reduced polymerisation of fibronectin. Alternatively, transglutaminase activity may be measured by the incorporation of [$^{14}$C]-putrescine incorporation into N,N'-dimethylcasein, as outlined by Lorand et al., 1972, Analytical Biochemistry 50, 623. The increased ability of the variant enzyme to facilitate the adhesion and spreading of cells on medical implants may be measured by the methods disclosed herein.

Variant transglutaminases may be made using methods of protein engineering and site-directed mutagenesis commonly known in the art (for example, see Sambrook et al. (1989) Molecular Cloning, A Laboratory Manual, Second Edition, Cold Spring Harbor, N.Y.).

Preferably, the variant mammalian transglutaminase is an inactive tissue transglutaminase wherein its active site cysteine (e.g. Cys 277 of human tissue transglutaminase; see Gentile et al. 1992 supra and accession no. M 55153) is mutated to a serine residue.

Advantageously, the variant mammalian transglutaminase is a fragment of a naturally occurring tissue transglutaminase or Factor XIIIa which retains the ability of said naturally occurring transglutaminase to promote biocompatibility. The ability of transglutaminase fragments to promote biocompatibility may be determined by measuring the adhesion properties of such variant proteins, e.g. by coating artificial polymers with the variant enzyme(s), with or without precoating with fibronectin, and then investigating the ability of cells to attach to and spread on these coated polymers.

It will be appreciated by those skilled in the art that the medical implant materials of the invention may comprise naturally occurring polymers, synthetic polymers, co-polymers of such polymers, and blends thereof.

Preferably, the polymer is a naturally occurring polymer. More preferably, the polymer is a naturally occurring extracellular matrix molecule such as collagen, fibronectin, fibrin, fibrillin, glycosoaminoglycans, and hyaluronic acid.

Advantageously, the polymer is a synthetic polymer. More preferably, the polymer is a synthetic polymer selected from the group consisting of poly(ε-caprolactone) (PCL), poly(L-lactide) (PLA), poly(glycolide) (PGA), poly(DL-lactide co-glycolide) (PLG) and copolymers and blends thereof. Other synthetic polymers include methacrylates poly(ethylmethacrylate), ethylacrylate, tetrahydrofurfurylmethacrylate, hydroxyethylmethacrylate, silastic, poly(tetrafluoroethylene), medpore (porous polyethylene), poly(orthoester), and poly(dioxane).

Most preferably, the medical implant material comprises poly-(ε-caprolactone).

It will be appreciated that the polymers may be biodegradable or non-biodegradable. Preferably, the polymer is biodegradable. More preferably, the polymer is a biodegradable polymer which has a biodegradation rate that is the same as or slower than the rate of regeneration of the tissue for which the medical implant acts as a temporary replacement. Thus, the biodegradable polymer should be resorbed only after it has served its purpose as a scaffold for regeneration of new tissue. It will be further appreciated that the polymer and its degradation product(s) should be substantially non-toxic and non-inflammatory.

In the medical implant material according to the first aspect of the invention, the polymer provided is associated with a binding protein which binds a transglutaminase.

By a 'binding protein' we include a protein or polypeptide which is able to bind to a mammalian transglutaminase, i.e. a transglutaminase binding protein. Preferably, the transglutaminase binding protein binds to the mammalian transglutaminase with a binding affinity greater than $10^3$ L/mol. More preferably, the affinity constant is greater than $10^4$ L/mol, for example greater than $10^5$ L/mol, $10^6$ L/mol, $10^7$ L/mol, $10^8$ L/mol, $10^9$ L/mol, $10^{10}$ L/mol, or $10^{11}$ L/mol.

Advantageously, the transglutaminase binding protein is or comprises a transglutaminase substrate.

By 'a transglutaminase substrate' we include a protein or polypeptide which comprises a transglutaminase substrate site.

Preferably, the transglutaminase binding protein is selected from a group of transglutaminase substrates of consisting fibronectin, fibrin, fibrinogen, collagen, entactin, osteonectin, osteopontin, thrombospondin, vitronectin, β-lactoglobulin and casein, or fragments thereof that are capable of binding to a transglutaminase.

More preferably, the transglutaminase binding protein is fibronectin or a fragment thereof that is capable of binding to a transglutaminase.

Most preferably, the transglutaminase binding protein is a human fibronectin fragment comprising the N-terminal fragment of fibronectin (i.e. amino acids 32-608) or fragments within this domain, for example the probable tTgase binding site (amino acids 229-273), the collagen binding site (amino acids 308-608) or the fibrin-Heparin binding site1 (amino acids 52-272) or combinations of these different fragments. From GenBank X02761 (Reference Kornblititt et al EMBO. J. (1985) 4, 1755-1759) for human fibronectin.

It will be appreciated by those skilled in the art that particular combinations of transglutaminase and transglutaminase binding protein may be preferred. For example, it may be preferable to use a tissue transglutaminase in combination with fibronectin (or a fragment thereof). Likewise, it may be preferable to use a plasma transglutaminase (e.g. Factor XIII) in combination with fibrin (or a fragment thereof) and fibronectin (or a fragment thereof). Additionally, the medical implant materials of the first aspect of the invention may comprise mixtures of different transglutaminases and transglutaminase binding proteins.

In the medical implant materials of the present invention, the polymer may be associated with the transglutaminase binding protein using methods known in the art. By 'associated with' we include a polymer which is coated, impregnated, covalently bound to or otherwise admixed with a transglutaminase binding protein.

Preferably, the polymer is coated with the binding protein. By 'coated' we mean that the transglutaminase binding protein is applied to the surface of the polymer. Thus, the polymer may be painted or sprayed with a solution comprising a transglutaminase binding protein. Alternatively, the polymer may be dipped in a reservoir of transglutaminase binding protein solution. Preferably, the polymer is pre-shaped to from the medical implant prior to being coated with a transglutaminase binding protein.

Advantageously, the polymer is impregnated with the binding protein. By 'impregnated' we mean that the transglutaminase binding protein is incorporated or otherwise mixed with polymer such that it is distributed throughout the medical implant material.

For example, the polymer may be incubated overnight at 4° C. in a solution comprising a transglutaminase binding protein. Alternatively, a transglutaminase binding protein may be immobilised on the polymer surface by evaporation or by incubation at room temperature.

In an alternative embodiment, the transglutaminase binding protein is covalently linked to the polymer, e.g. at the external surface of the polymer.

Thus, a covalent bond is formed between an appropriate functional group on transglutaminase binding protein and a functional group on the polymer support. Methods for covalent bonding of proteins to polymer supports fall into a number of sub-groups including covalent linking via a diazonium intermediate, by formation of peptide links, by alkylation of phenolic, amine and sulphydryl groups on the binding protein, by using a poly functional intermediate e.g. glutardialdehyde, and other miscellaneous methods e.g. using silylated glass or quartz where the reaction of trialkoxysilanes permits derivatisation of the glass surface with many different functional groups. For details, see Enzyme immobilisation by Griffin, M., Hammonds, E. J. and Leach, C. K. (1993) In *Technological Applications of Biocatalysts* (BIOTOL SERIES), pp. 75-118, Butterworth-Heinemann. See also the review article entitled 'Biomaterials in Tissue Engineering' by Hubbell, J. A. (1995) *Science* 13:565-576.

Once associated with the polymer, the transglutaminase binding protein may provide a means of linking the mammalian transglutaminase to the polymer.

The polymer associated with the binding protein may be treated with the mammalian transglutaminase using the same methods described above. Thus, the polymer (or medical implant material comprising said polymer) may be coated, impregnated, covalently bound to or otherwise admixed with a mammalian transglutaminase.

Preferably, the polymer is coated with a mammalian transglutaminase. For example, the polymer may be painted or sprayed with a solution comprising a transglutaminase. Alternatively, the polymer may be dipped in a reservoir of transglutaminase solution. More preferably, the polymer is coated with a transglutaminase immediately prior to implantation of the medical implant material into the human or animal host. For example, the polymer may be coated with the transglutaminase on the same day that the medical implant is to be used, for example about one hour before implantation.

Advantageously, the polymer is impregnated with a mammalian transglutaminase.

Conveniently, the polymer is covalently bound to a mammalian transglutaminase, either directly or indirectly via the binding protein.

It will be appreciated that the transglutaminase binding protein may be coated, impregnated, covalently bound to or otherwise admixed with the polymer at the same time as or prior to treating the polymer with a mammalian transglutaminase. Preferably, the polymer is associated with the binding protein prior to being treated with a mammalian transglutaminase.

In a preferred embodiment of the invention, there is provided a medical implant material comprising a polymer which is first coated with a transglutaminase binding protein and then coated with a mammalian transglutaminase.

In the medical implant materials according to the first aspect of the invention, the transglutaminase is provided in the absence of free divalent metal ions.

The presence of free divalent metal ions, e.g. $Ca^{2+}$ ions, plays a key role in the regulation of mammalian transglutaminase activity. Thus, absence of free divalent metal ions from the vicinity of the transglutaminase renders the enzyme substantially inactive in vitro.

By 'in the absence of' we include environments wherein the concentration of free divalent metal ions, such as $Ca^{2+}$ ions, is less than 10 μM. Preferably the concentration is less than 1 μM.

Preferably, the transglutaminase is provided in the absence of free $Ca^{2+}$ ions.

In a preferred embodiment of the first aspect of the invention, free divalent metal ions are reduced or eliminated from the vicinity of the transglutaminase by the inclusion in the medical implant material of a chelating agent.

For example, the medical implant materials may comprise a polymer that has been dipped in a solution comprising a transglutaminase and a chelating agent, such that the polymer is coated in the transglutaminase and chelating agent.

Preferably, the chelating agent is EDTA or EGTA.

More preferably, the medical implant material is provided with EDTA or EGTA at a concentration of between 5 mM and 0.1 M.

In yet another preferred embodiment of the first aspect of the invention, the medical implant material further comprises a reinforcing agent.

The reinforcing agent may be any substantially non-toxic material that can be blended or mixed with the polymer/transglutaminase components of the medical implant material to increase its strength.

Preferably, the reinforcing agent is selected from a group consisting of alumina, alumina-boria-silica, calcium metaphosphate glass fibres, titanium and carbon.

It will be appreciated by those skilled in the art that the medical implant materials of the invention may further comprise one or more additional polymer(s). Thus, there is provided a medical implant material comprising a copolymer or blended polymers and a mammalian transglutaminase.

Conveniently, the one or more additional polymer is a synthetic polymer.

Advantageously, the one or more additional polymer is a natural polymer.

Preferably, the one or more additional polymer is a natural polymer selected from the group consisting of collagen, fibronectin, fibrin, fibrillin, hyaluronic acid and glycosaminoglycans.

A second aspect of the invention provides the use of a mammalian transglutaminase in a method for improving the biocompatibility of a medical implant material, the method comprising the steps of:
(i) providing a medical implant material comprising with a polymer associated with a binding protein for binding the transglutaminase; and
(ii) treating said material with a mammalian transglutaminase.

By 'biocompatibility' we mean the ability of the medical implant material to facilitate its colonisation by host cells and to enhance proliferation of host cells therein. Thus, biocompatibility is not intended to cover mere adhesion of host cells to the medical implant material, but rather relates to an interaction between the host cells and implant materials which permits colonisation to occur. In particular, biocompatibility includes the ability of said material to support cell attachment, cell spreading, cell proliferation and differentiation.

Biocompatibility of a medical implant material may be assessed using methods known in the art (see Examples). For example, increased biocompatibility of a medical implant material is associated with an increase in the ability of the material to facilitate cell attachment, cell spreading, cell proliferation and differentiation. In addition, the material should not induce any substantial loss in cell viability, i.e. via the induction of cell death through either apoptosis or necrosis. The differentiation of a cell type is measured in different ways depending on the cell type in question For example, for osteoblasts cells in culture, alkaline phosphate together with extracellular matrix (ECM) deposition, e.g. collagen 1, fibronectin, osteonectin and osteopontin, can be used as a marker. In addition, the ability of cells to proliferate and deposit ECM is important to ally material that is to be used as an implant, this includes endothdelial cells, chondrocytes and epithelial cells etc.

A preferred embodiment of the second aspect of the invention provides the use of a mammalian transglutaminase to facilitate colonisation of a medical implant material by host cells.

The mammalian transglutaminase for use in the second aspect of the invention pay be any transglutaminase described in relation to the first aspect of the invention. Preferably, the transglutaminase is a tissue transglutaminase. Advantageously, the transglutaminase is derived from human tissue or cells. Suitably, the transglutaminase is a recombinant transglutaminase. Conveniently, the transglutaminase is a variant transglutaminase.

The second aspect of the invention provides the use of a mammalian transglutaminase to improve the biocompatibility of any material comprising a polymer associated with a transglutaminase binding protein that may have utility in medical implants.

Preferably, the medical implant material is or comprises a polymer as defined above in relation to the first aspect of the invention.

Thus, the medical implant material may comprise a naturally occurring polymer, for example a naturally occurring polymer selected from the group consisting of extracellular matrix molecules such as collagen, fibronectin, fibrin, fibrillin glycosaminoglycans, and hyaluronic acid.

Alternatively, or in addition, the medical implant material may comprise a synthetic polymer, for example a polymer selected from the group consisting of poly(ε-caprolactone) (PCL), poly(L-lactide) (PLA), poly(glycolide) (PGA), poly($_{DL}$-lactide co-glycolide) (PLG) and co-polymers and blends thereof. Other synthetic polymers include methacrylates poly (ethylmethacrylate), ethylacrylate, tetrahydrofurfuryl-methacrylate, hydroxyethylmethacrylate, silastic, poly(tetrafluoro-ethylene), medpore (porous polyethylene), poly (orthoester), and poly(dioxane).

Preferably, the medical implant material is or comprises the polymer poly-ε-caprolactone).

In the use according to the second aspect of the invention, treatment of the medical implant material with a mammalian transglutaminase may comprise coating, impregnating, covalently linking or otherwise mixing the medical implant material with the transglutaminase.

Preferably, step (ii) comprises coating the medical implant material with a transglutaminase. In an alternative embodiment, step (ii) comprises impregnating the medical implant material with a transglutaminase. In a further embodiment, step (ii) comprises covalently linking the transglutaminase to the medical implant material (see above methods).

Advantageously, the step of treating the medical implant material with a transglutaminase is carried out in the absence of free divalent metal ions, such that the transglutaminase is substantially inactive in vitro.

For example, the step of treating the medical implant material with a transglutaminase is carried out in the presence of a divalent metal ion chelating agent, such as EDTA or EGTA.

In the second aspect of the invention, the medical implant material comprises a polymer associated with a transglutaminase binding protein. The polymer and binding protein may be associated in a variety of ways as described in relation to the first aspect of the invention.

As in the case of the first aspect of the invention, it will be appreciated by persons skilled in the art that certain combinations of transglutaminases and transglutaminase binding proteins may be preferentially used, for example a tissue transglutaminase with fibronectin (or a fragment thereof) or a plasma transglutaminase with fibrin (or a fragment thereof). Additionally, mixtures of different transglutaminases and transglutaminase binding proteins may be utilised.

A preferred embodiment of the second aspect of the invention provides the use of a mammalian transglutaminase to improve the biocompatibility of a medical implant material further comprising a reinforcing agent.

Advantageously, the reinforcing agent is selected from a group consisting of alumina, alumina-boria-silica, calcium metaphosphate glass fibres, carbon and titanium.

A further preferred embodiment of the second aspect of the invention provides the use of a mammalian transglutaminase to improve the biocompatibility of a medical implant material further comprising one or more additional polymer(s). Thus, the medical implant material may be a copolymer or a blend of polymers.

Conveniently, the one or more additional polymer is a synthetic polymer. Advantageously, the one or more additional polymer is a natural polymer. Preferably, the one or more additional polymer is a natural polymer selected from the group consisting of collagen, fibronectin, fibrin, fibrillin, hyaluronic acid and glycosaminoglycans.

In a preferred embodiment of the first or second aspect of the invention, the medical implant material is artificial bone.

The invention will now be described in detail with reference to the following figures and examples:

DETAILED DESCRIPTION OF THE INVENTION

EXAMPLES

Materials and Methods

Poly(ε-Caprolactone) Disc Preparation

Figure 1:
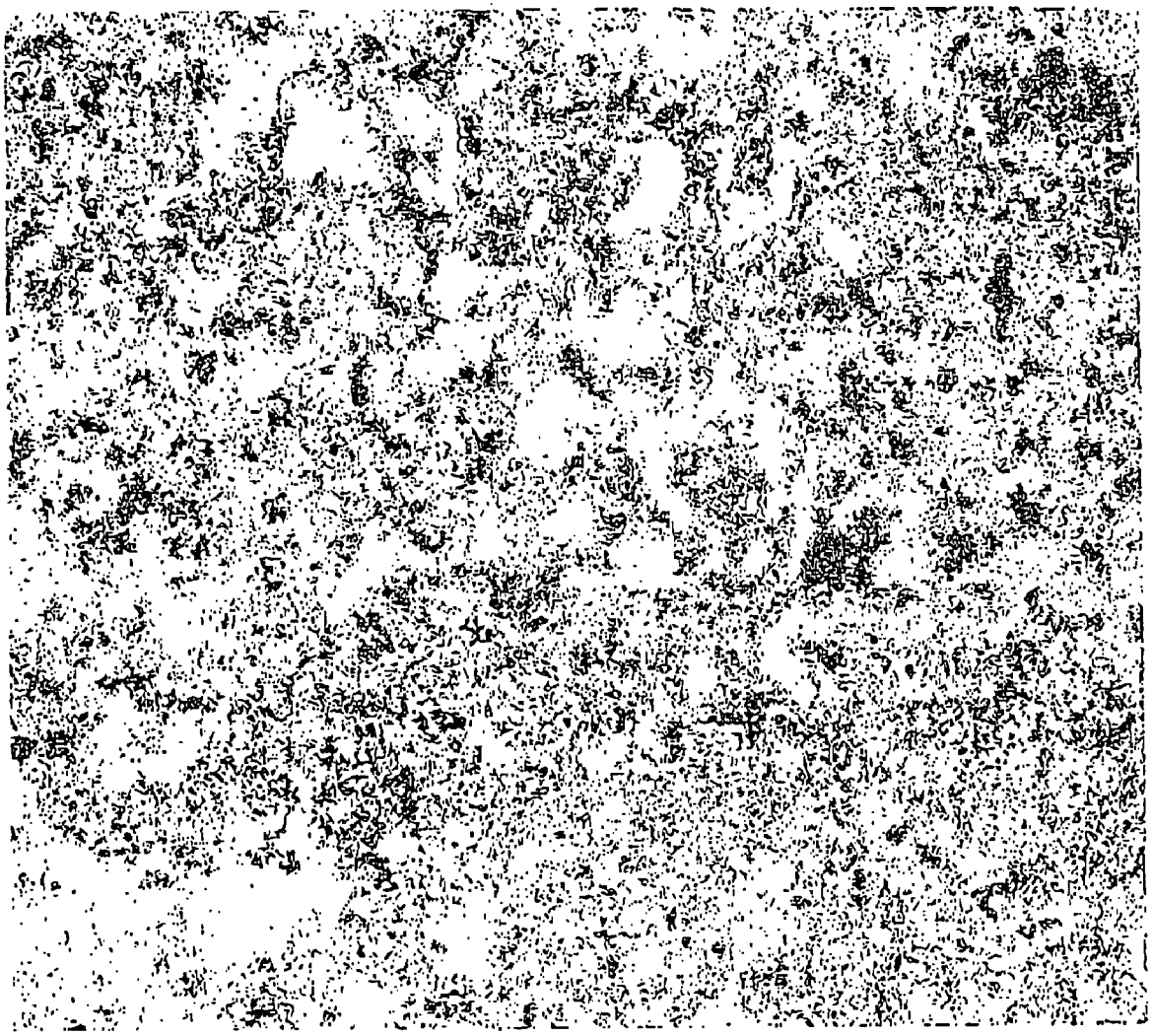
FIG. 1 shows a photograph of the morphology of human osteoblast cells (HOBs) on PCL after 24 hours when seeded in 10% serum containing medium (viewed using light microscopy, original magnification was ×63).

Poly(ε-caprolactone)(PCL)(PCL650; Solvay Interox) was purchased in pellet form and pressed in a square cavity at a temperature above melting point, in order to form a 4 mm thick meet. PCL discs (6 mm in diameter) were then stamped from the polymer sheet using a cork borer and sterilised under UV light for 1 hour each side prior to use.

Cell Culture

Human Osteoblast (HOB) cells were isolated from explants of trabecular bone dissected from femoral heads following orthopaedic surgery (as described by DiSilvio, 1995). All cells were cultured in vitro using Dulbecco's Modified Eagles Medium (DMEM). This was supplemented with 10% foetal calf serum, 1% non-essential amino acids, 150 µg/ml ascorbic acid (BDH, Poole, U.K.), 2 mM L-Glutarine, 0.02M [4-(2-hydroxyethyl)-1-piperazineethanesulfonic acid], (HEPES), 1% Penicillin/Streptomycin (all obtainable from Gibco, BRL, Paisley, U.K.). The cells were incubated at 37° C. in 5% $CO_2$, 95% air.

Visualisation of Human Osteoblasts Cells on PCL Over 4 Days Using the Toluidine Blue Stain and Transmission Electron Microscopy (T.E.M)

HOB cells were grown on the PCL in 10% serum containing DMEM to initially assess the interaction of cells with this particular polymer surface. The toluidine blue stain allowed the attachment, spreading and proliferation of the cells-on the PCL to be observed. T.E.M. allowed the ultra structure of the cells to be observed on the biomaterial. Both these techniques would indicate whether the polymer is biocompatible with this particular cell type.

Toluidine Blue

PCL discs were placed in a 96 well plate (3 replicates per sample) and human osteoblast cells (HOBs) were seeded onto the biomaterial in 10% serum containing DMEM at a density of $1.7 \times 10^5 / cm^2$. Tissue culture plastic (TCP) was used as a positive control surface. The plate was then incubated at 37° C. in 5% $CO_2$. At days 1 and 4 after cell seeding the medium was removed and the cells were washed in sterile phosphate buffered saline (PBS). The cells were fixed in 4% paraformaldehyde and 2% sucrose for five minutes at room temperatue and then washed twice in PBS. The cells were stained with 1% toluidine blue diluted in sterile PBS for five minutes at room temperature. The samples were then washed several times in PBS and viewed using light microscopy (Olympus SZ-PT).

Transmission Electron Microscopy (T.E.M.)

PCL discs were placed in a 48-well plate (3 replicates per time point) and HOB cells were seeded onto the biomaterial in 10% serum containing DMEM at a density of $1.7 \times 10^5 / cm^2$. Thermanox was used as a positive control spice. The plate was then incubated at 37° C. in 5% $CO_2$. At days 1, 2, 4 and 8 days after cell seeding, the medium was removed and the cells were washed in sterile PBS. The samples were fixed overnight in 1.5% glutaraldehyde in 0.1 M sodium cacodylate buffer (pH 7,4) then washed in the same buffer and secondary fixed using 1% osmium tetroxide in Millonig's buffer for 1 hour. The samples were washed in buffer followed by a dehydration step through a series of alcohols, 50%, 70%, 90%, 96% and 100% with two 10-minute changes for each alcohol and 30 minutes in 100% alcohol. Araldite CY212 resin was added to give a ratio 3:1 with alcohol, fixed for 1 hour and then transferred to a 1:1 resin:alcohol mixture and left overnight and then placed in pure resin for 2 hours under vacuum inltration. The pure resin was changed twice (2 hours each change) and then made into blocks. The polymers were then embedded and cured at 45° C. in an oven for 48 hours (this temperature was used to prevent the PCL from melting). Ultra thin sections were then cut using a Reichert Ultracut E Ultramicrotome, collected on copper grids and stained with 3% Uranylacetate in 50% methanol for 6 minutes and then Reynold's lead citrate for 6 minutes. The samples were examined using a Philips EM410 transmission electron microscope at 80 kV.

Guinea-Pig Liver Tissue Transglutaminase Type II Immobilisation onto PCL

Guinea-pig liver tissue transglutaminase (i.e. type II transglutaminase, tTG) obtainable from Sigma was immobilised onto PCL using three methods as shown below. Each method uses the idea of immobilising the tTG to the PCL via fibronectin because fibronectin has a tTG binding site. The tTG does not have to be active to bind to fibronectin (i.e. calcium ions are not required). Ethylenediaminetetraacetic acid (EDTA) was added to the tTG to keep the enzyme in its inactive form and prevent the enzyme from cross-linking the fibronectin or itself during the immobilisation. The tTG could be added to the PCL in drop form because the surface of the PCL was hydrophobic. A quantity of 60 µl was enough to cover the whole surface, forming a meniscus on the surface.

(i) Immobilisation at 4° C.

A solution of 15 µg/ml bovine plasma fibronectin (Gibco) and 10 µg/ml tissue transglutaminase (tTG) in 0.1M EDTA (pH 7.4.), was added to the sterile PCL discs (60 µl per disc). This was then left overnight at 4° C. After incubation, the solution was removed and the PCL was washed three times with 0.1M Tris-HCl (pH 7.4.), 5 minutes each wash. The discs were then transferred to the tissue culture plates.

(ii) Immobilisation by Evaporation Overnight

A 60 µl aliquot of 30 µg/ml bovine plasma fibronectin in sterile distilled water was added to each sterile PCL disc and left overnight in the tissue culture hood to evaporate. Once the water had evaporated, a 60 µl aliquot of 20 µg/ml tissue transglutaminase in 5 mM EDTA (pH 7.4.) was added to the PCL. This was left to evaporate overnight in the tissue culture hood and then the discs were washed three times in 0.1M Tris-HCl (pH 7.4.), 5 minutes each wash. The discs were then transferred to the tissue culture plates.

(iii) Immobilisation by Incubation at Room Temperature

A 60 µl aliquot of 30 µg/ml bovine plasma fibronectin in sterile distilled water was added to each sterile PCL disc and left overnight in the tissue culture hood to evaporate. Once the water had evaporated, a 60 µl aliquot of 20 µg/ml tissue transglutaminase in 5 mM EDTA (pH 7.4.) was added to each PCL disc. This was then left for one hour at room temperature. The tTG solution was removed and then the discs were washed three times in 0.1M Tris-HCl (pH 7.4.), 5 minutes each wash and transferred to the tissue culture plates.

ELISA for Fibronectin

PCL discs were coated with different concentrations of fibronectin (0 to 50 µg/ml) by the evaporation technique described above. The fibronectin was detected using the fibronectin ELISA assay (Gaudry, 1998). The polymers were initially washed in 3×100 µl of PBS and then blocked with 100 µl of 3% w/v bovine serum albumin (BSA) in PBS. The plate was incubated for 1 hour at room temperature and then washed with 3×100 µl of PBS before the addition of 100 µl of the primary antibody (polyclonal rabbit anti-human plasma fibronectin, diluted 1:5000 in blocking buffer). The plate was incubated for 2 hours at room temperature, then washed in 3×100 µl of PBS before the addition of 100 µl of the secondary antibody (HRP conjugated goat anti-rabbit, diluted 1:5000 in blocking buffer). The plate was incubated for 1 hour at room temperature and then rinsed in 3×100 µl of before the addition of 100 µl of 0.1M sodium acetate. The HRP was detected using 100 µl of the developer (20 mls NaOAc, 150 µl TMB and 10 µl $H_2O_2$) and the reaction stopped with 50 µl of 2.5M $H_2SO_4$. The results were then read in a colourimeter (Titertek Multiskan MCC/340MK2) at a wavelength of 450 nm.

Fibronectin-ELISA for Tissue Transglutaminase

The ELISA used to detect tTG was a modification of that developed by Achyuthan et al., (1995). This relies upon the ability of tTG to bind specifically to immobilised plasma fibronectin.

PCL discs were coated with 60 µl of 30 µg/ml fibronectin in sterile distilled water and then different concentrations of tTG (0-50 µg/ml) using the two different methods as described above. The discs were washed in 3×100 µl of PBS and then blocked with 100 µl of 3% w/v BSA in PBS for 1 hour at room temperature. The PCL discs were rinsed with 3×100 µl of PBS and bound tTG was detected using 100 µl of anti-monoclonal antibody CUB7402 (diluted 1:1000 in blocking buffer). The primary antibody was left on the polymers for 2 hours at room temperature and then washed in 3×100 µl of PBS prior to the addition of 100 µl of the secondary antibody (HRP-conjugated goat-anti-mouse IgG (Sigma) diluted 1:5000 in blocking buffer). This was left for 1 hour at room temperature and then the HRP detected (as described above).

To Determine if tTG is in its Active Form when Immobilised on the PCL Surface

To determine if fibronectin and tTG are present on the surface of PCL, the biotin-cadaverine assay was used, (Jones et al., 1997). This method also allows the activity of tTG on the surface of the biomaterial to be quantified.

Four tissue culture plastic (TCP) wells and 4 PCL discs were coated with fibronectin as described above (3 replicates per sample were used). For one of the fibronectin coated PCL samples, tTG was immobilised onto the PCL surface using either of the three different methods also described above. After washing the fibronectin/tTG coated PCL in 3×100 µl of 0.1M Tris-HCl (pH, 7.4.), 100 µl of homogenising buffer consisting of 0.25 mM sucrose, 5 mM Tris-HCl (pH 7.4.) and 2 mM EDTA (H 7.4.) was added and incubated for different time periods up to 15 hours at 37° C. This was then tested for tTG activity. The other three fibronectin coated PCL discs were used for controls, which consisted of adding tTG in directly homogenising buffer containing either calcium (positive control) or EDTA (negative control). The other negative control was homogenising buffer only. The four TCP wells coated with fibronectin were to enable tTG activity to be analysed in the homogenising buffer taken from the fibronectin/tTG coated PCL surface and for three controls which are the same as mentioned above.

The PCL or TCP were initially blocked with 100 µl of 3% BSA in 0.1M Tis-HCl (pH 7.4.) at room temperature for 1 hour and then washed with 3×100. µl of 0.1M Tris-HCl. For the positive controls, 100 µl of the following solution was added to the fibronectin coated TCP and PCL: 20 µg/ml guinea pig tTG, 5 mM $CaCl_2$, 3.85 mM DTT and 0.4% biotin-cadaverine in homogenising buffer. For the negative controls 100 µl of the following solution was added to the fibronectin coated TCP and PCL: 20 µg/m guinea pig tTG, 5 mM EDTA, 3.85 mM DTT and 0.4% biotin-cadaverine in homogenising buffer. To rule out any biomaterial interaction with the assay, another control was used which consisted of adding the following solution to fibronectin coated PCL and TCP: 5 mM $CaCl_2$, 3.85 mM DTT and 0.4% biotin-cadaverine in homogeising buffer. This was also added to the fibronectin and tTG coated PCL. To the 100 µl of homogenising buffer that had been incubated with the immobilised fibronectin/tTG surface, 10 mM $CaCl_2$, 3.85 mM DTT and 0.4% BC was added.

The samples were then left for 2 hours at 37° C. After this time 100 µl of 5 mM EDTA in 0.1M Tris-HCl was added to the wells, left for 10 minutes and then washed in 2×100 µl of 0.1M Tris-HCl. 100 µl of extravidin peroxidase in 3% BSA was added (1:5000 dilution) and left at 37° C. for 1 h. The wells were washed with 3×100 µl of 0.1M Tris-HCl and 100 µl of 0.1M NaOAc (pH 6.0). 100 µl of the developer was added (20 mls NaOAc, 150 µl TMB and 10 µl $H_2O_2$) and the reaction stopped with 50 µl of 2.5M $H_2SO_4$. The results were then read in a colourimeter at a wavelength of 450 nm.

To Determine the Effect Tissue Transglutaminase has on the Spreading of Human Osteoblast Cells on Poly(ε-Caprolactone)

Initially sterile PCL discs were coated with fibronectin and tTG as described above. Controls consisted of PCL, PCL coated with fibronectin and TCP. The HOB cells were harvested using trypsin, followed by blocking in serum containing medium and then resuspended twice in serum free medium. Cells were seeded onto the samples at $3.4 \times 10^5$ cells/$cm^2$ in serum free medium. Cells were also seeded onto TCP in serum continuing medium (positive control surface). All samples were done in triplicate.

Scanning Electron Microscopy

At 1, 2, 4 and 6 hours, the samples were washed twice with PBS and fixed in 1.5% paraformaldehyde in sodium cocodylate buffer for 30 minutes at room temperature. The samples were dehydrated in a graded series of ethanol (60-100%) and then left to evaporate in hexomethyldisiazane (HMDS) overnight. The samples were then gold coated and viewed using a Philips 501B scanning electron microscope.

Environmental Scanning Electron Microscopy

At 30 minutes, 1 hour and 3 hours the samples were washed in $2 \times 200$ μl of PBS and fixed in 200 μl of 1.5% paraformaldehyde in 0.1M sodium cocodylate buffer (pH 7.4.) for 30 minutes at room temperature. The cells were then washed in $2 \times 200$ μl of sterile double distilled water and viewed using a Philips XL 30 environmental scanning electron microscope equipped with a field emission gun (FEG-ESEM) in wet mode. The degree of cell spreading was scored as type I-III (Sinha et al., 1994).

To Determine the Effect Tissue Transglutaminase has on the Differentiation of Human Osteoblast Cells on Poly(ε-Caprolactone)

(i) Determination of the Minimum Amount of Foetal Calf Serum in DMEM Required to Stimulate Human Osteoblast Cell Proliferation on PCL Initially, the minimum amount of foetal calf serum (FCS) in the medium required to stimulate HOB cell proliferation was determined. The cells were harvested using trypsin, followed by blocking in serum containing medium and then resuspended twice in serum free medium. The cells were then seeded into a 96 tissue culture plate (Falcon) in either, 100 μl of 0%, 2%, 4%, 6% or 10% FCS at a density of $1.7 \times 10^5$ cells/$cm^2$. The negative control used. consisted of medium without cells, and the positive control consisted of cells in 10% serum containing medium. The cells were incubated at 37° C., 5% $CO_2$ for either 1, 2, 4, 6 or 8 days. At each of these time points the medium was removed from the wells and the cells washed in $2 \times 100$ μl of sterile PBS. 100 μl of sterile double distilled water was added to each well and the cells lysed by the freeze thaw method, which involved placing the samples at −80° C. for 20 minutes and then at 37° C. for 15 minutes. This was repeated three times. The DNA content of each sample was determined using the DNA Hoechst assay (Rago et al., 1990) (see below).

The above experiment was repeated using PCL instead of TCP, however 7% and 10% FCS in the medium was used and the cells were incubated for either 1 or 3 days. The negative control consisted of medium without cells. The positive control consisted of cells in 10% serum containing medium on TCP.

(ii) DNA Hoechst Assay (Rago et al., 1990)

This assay allows cellular DNA content to be Wed using the fluorochrome; bisbenzimidazole (Hoechst 33258; Sigma). It works by a shift in the emission wavelength of Hoechst 33258 upon binding of cellular DNA. This results in a linear relationship between fluorescence and DNA content over a broad range of DNA. This reaction has been shown to be highly specific, and other cellular contents such as RNA, protein and carbohydrates do not cause significant fluorescence.

Hoechst 33258 was dissolved in sterile deionised water to a final concentration of 1 mg/ml and then diluted 1 in 50 with TNE buffer (pH 7.4.). TNE buffer consisted of 10mM Tris (BDH), 2 mM Sodium Chloride (Sigma) and 1 mM diaminoethanetetra-acetic acid (EDTA) (Fisons). It has previously been shown that crude cellular extracts assayed in the presence of high salt concentrations (as in the TNE buffer) yield higher fluorescence due to dissociation of DNA and chromatin with improved exposure of DNA binding sites.

100 μl of the diluted Hoechst 33258 was then added to 100 μl of the cell lysates along with a range of positive DNA calf thymus standards (range 0-20 μg/ml) (obtainable from Sigma). The fluorescence was then read at 360 nm (excitation filter) and 460 nm (emission filter) using a CytoFluor™ fluorescent plate reader (Millipore).

(iii) The Differentiation of Human Osteoblast Cells on the Fibronectin/Tissue Transglutaminase Coated PCL Using the Alkaline Phosphatase Assay The sterile PCL discs were coated with fibronectin and tTG as described in section 2.4.3. Controls consisted of PCL, PCL coated with FN and also TCP. The HOB cells were harvested using trypsin, followed by blocking in serum containing medium and then resuspended twice in serum free medium. Cells were seeded onto the polymers and TCP at $1.7 \times 10^5$ cells/$cm^2$ in 10% serum containing medium. The cells were incubated for 2 days at 37° C., 5% $CO_2$. After this dime period, the medium was removed, 100 μl of PBS added and then 100 μl of sterile distilled water added. The cells were lysed using the freeze thaw method, whereby the cells were frozen at −80° C. for 20 minutes and then thawed for 15 minutes at 37° C. (this was repeated three times). The samples were then diluted 1 in 2 with sterile double distilled water. The DNA Hoechst assay (see above) and the Alkaline Phosphatase assay were then performed on the cell lysates (see below).

(iv) Alkaline Phosphatase (ALP) Assay (Granutest Kit Obtainable from Merck)

Alkaline phosphatase (ALP) is a marker of early bone cell differentiation. This photometric assay allows ALP activity to be quantified. The principle of the assay is the conversion of 4-Nitrophenylphosphate (substrate) and water to phosphate and 4-Nitrophenolate in the presence of active ALP.

Twenty-five ml of buffer (pH 9.8) (containing 1.0 mol/l diethanolamine, 0.5 mmol/l $MgCl_2$ and 0.225 mol/l NaCl) was added to 0.35 g of the substrate (consisting of 255 μmol 4-Nitrophenylphosphate). 50 μl of this solution was then added to 50 μl of the cell lysate sample and the absorbance read in a cytofluorimeter (Anthos Labtec Instruments) at 450 nm (measuring filter) and 620 nm (reference filter).

Results

Human Osteoblast Morphology on Poly(ε-Caprolactone) (PCL)

Human osteoblast cells were grown on the PCL in 10% serum containing DMEM to initially assess the interaction of cells with this particular polymer surface. Toluidine blue staining allowed the attachment, spreading and proliferation of the cells on the PCL. to be observed. Transmission electron microscopy (T.E.M.) allowed the ultra structure of the cells to be observed in order to assess their response to the biomaterial surface. This would give an indication as to whether the polymer is biocompatible with this particular cell type.

Figure 2:
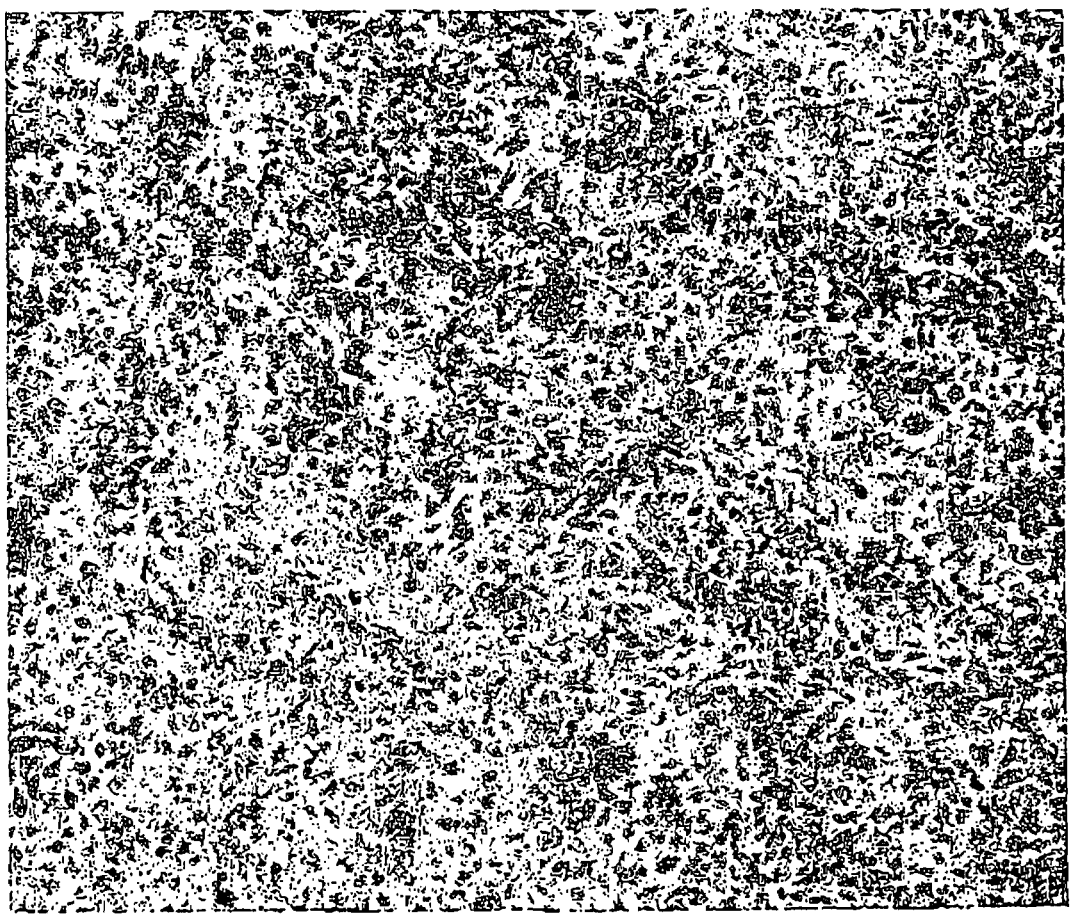
FIG. 2 shows a photograph of the morphology of human osteoblast cells on PCL after 4 days when seeded in 10% serum containing medium (viewed using light microscopy, original magnification was ×63).
Figure 3:
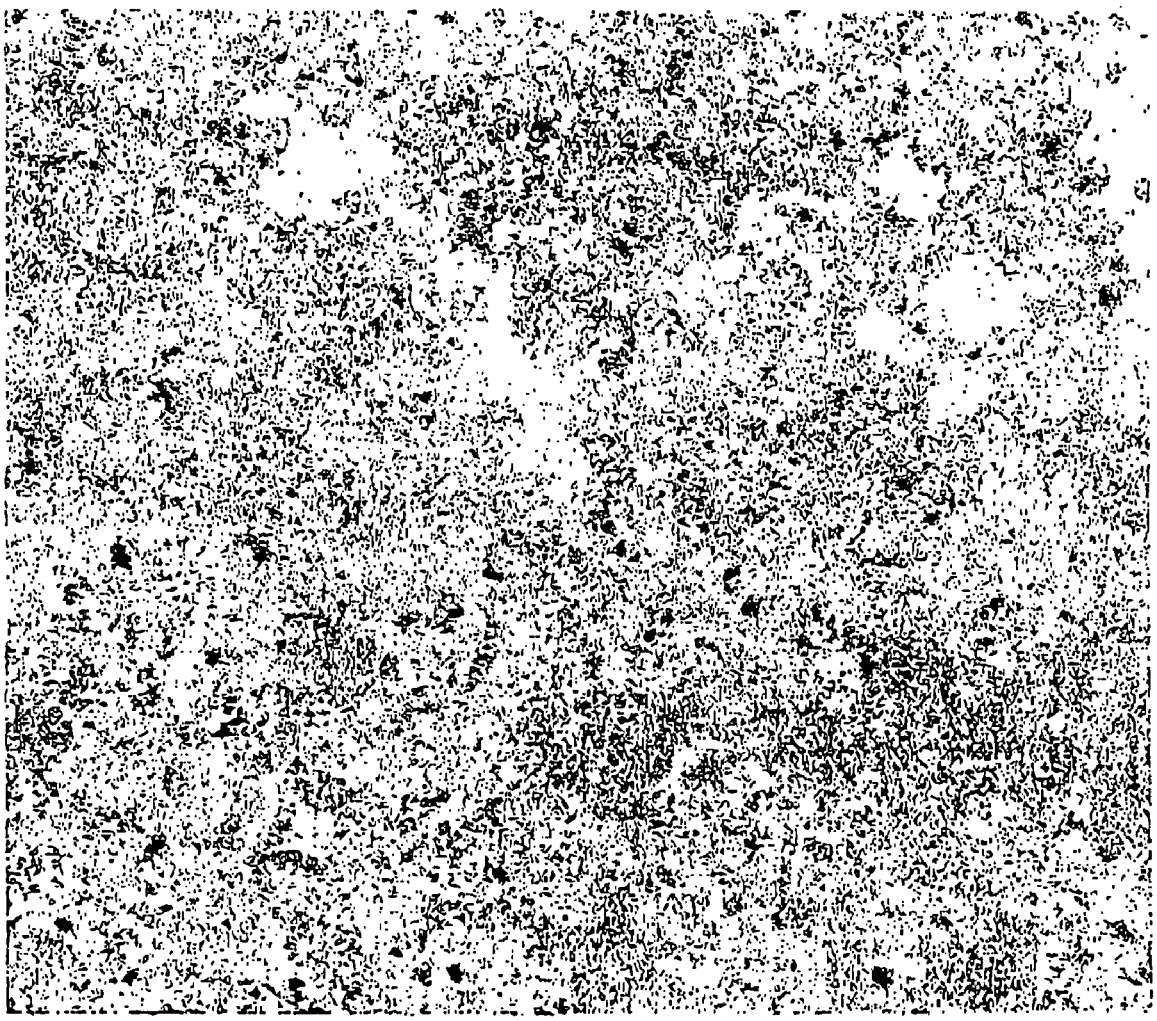
FIG. 3 shows a photograph of the morphology of human osteoblast cells on tissue culture plastic after 24 hours when seeded in 10% serum containing medium (viewed using light microscopy, original magnification was ×63).
Figure 4:
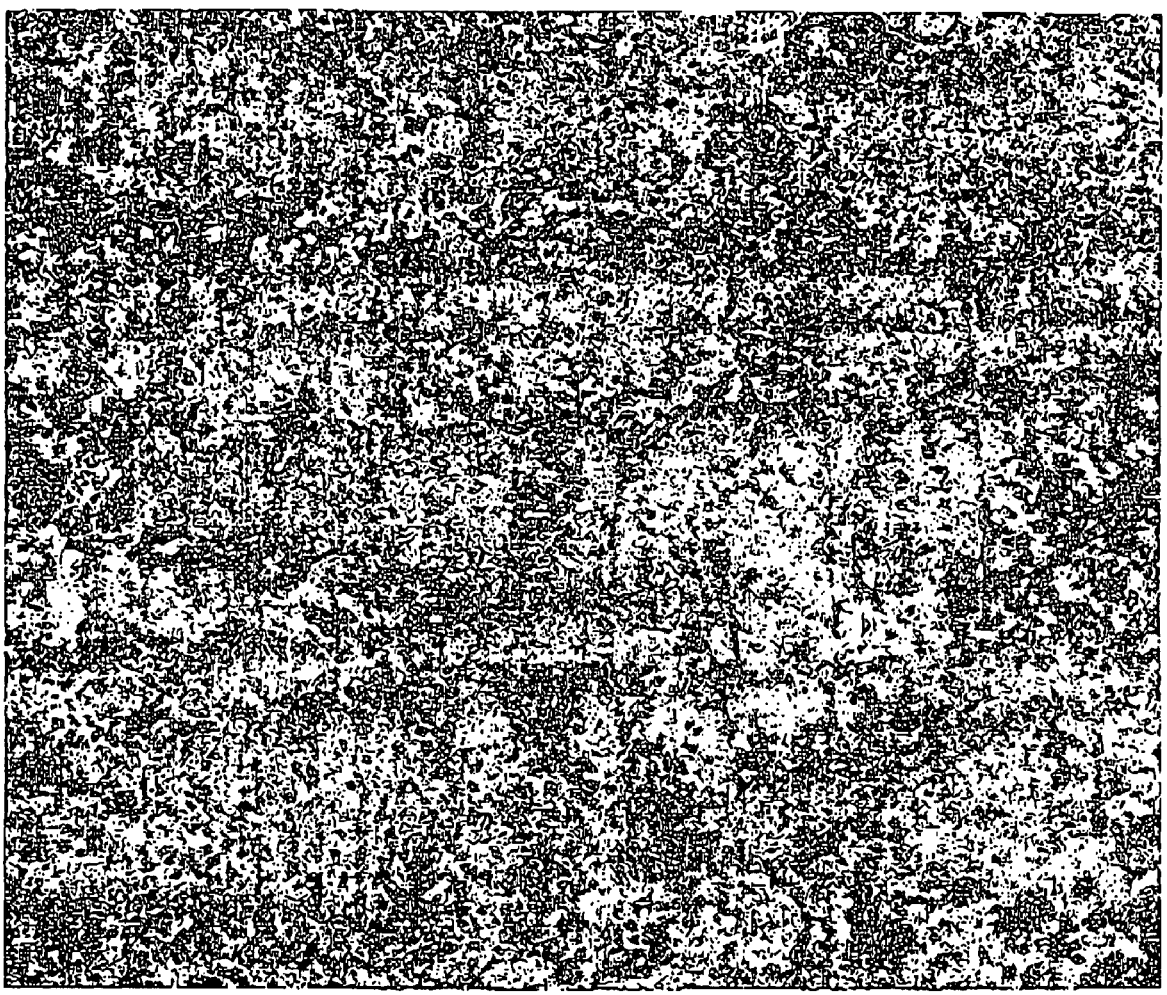
FIG. 4 shows a photograph of the morphology of human osteoblast cells on tissue culture plastic after 4 days when seeded in 10% serum containing medium (viewed using light microscopy, original magnification was ×63).

FIGS. 1 and 2 show HOB cells stained with toluidine blue at days 1 and 4 on PCL respectively. FIGS. 3 and 4 show HOB cells stained with toluidine blue at days 1 and 4 on TCP respectively. These results clearly indicate that HOB cells attach and spread on the PCL in DMEM containing 10% foetal calf serum as compared to the positive control (TCP). There is also a definite increase in cell population from day 1 to day 4 on both the TCP and PCL surfaces.

The T.E.M. results also indicated that the HOB cells proliferate on the PCL surface as shown by multilayer formation over time. The ultra structure of HOB cells on PCL was seen to be normal. However at 8 days of culture in DMEM containing 10% foetal calf serum, it was found that very few cells remained on the surface. It was thought that the cells must have been removed during the washing processes.

The Detection of Fibronectin and Tissue Transglutaminase (tTG) on PCL

Figure 5:
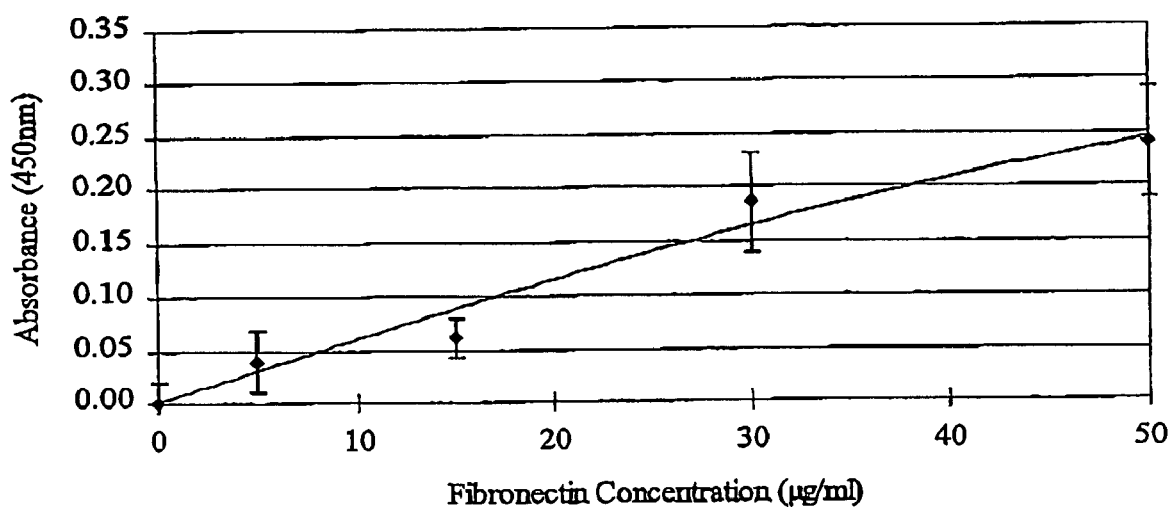
FIG. 5 shows the standard curve for the binding of fibronectin to poly($\epsilon$-caprolactone) (PCL) as measured using the ELISA technique (see Examples) The fibronectin was immobilised by evaporation overnight at room temperature (see section 2.4.2 for details). Data represent mean values +/−S.D. (n=3).

The ELISA technique clearly demonstrated the binding of fibronectin to PCL (see FIG. 5) The concentration of bound fibronectin increased proportionally up to 50 µg/ml.

Figure 6:
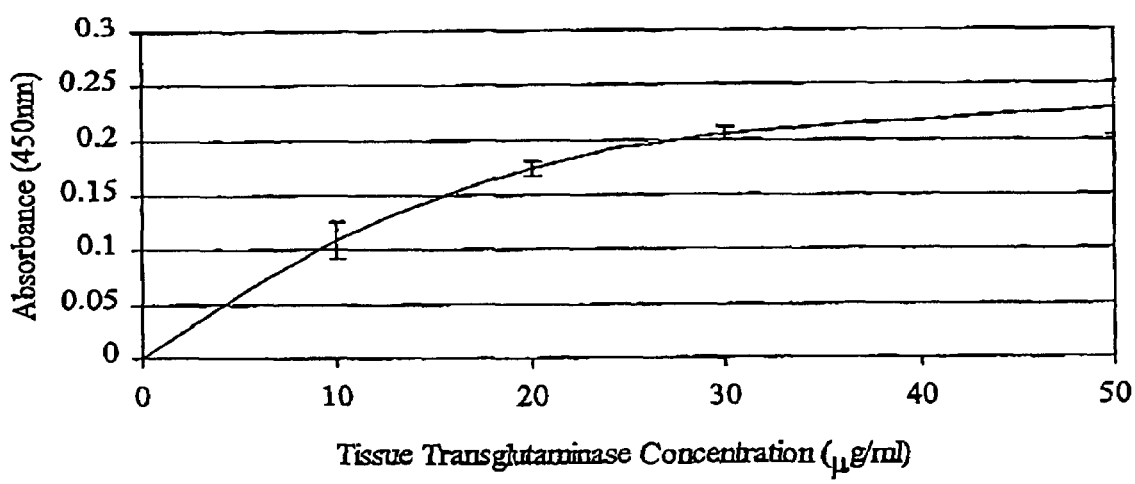
FIG. 6 shows the standard curve for the binding of tissue transglutaminase to fibronectin coated poly($\epsilon$-caprolactone) (PCL) as measured using the ELISA technique (see Examples). The tTG was immobilised by evaporation overnight at room temperature (see section 2.4.2. for details). Data represent mean values +/−S.D., (n=3).
Figure 7:
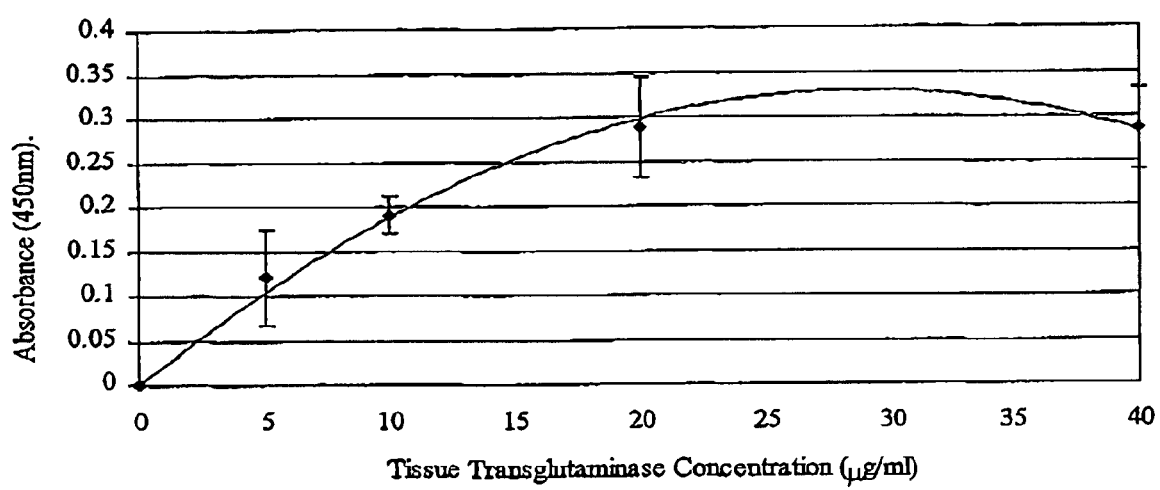
FIG. 7 shows the standard curve for the binding of tissue transglutaminase to fibronectin coated poly($\epsilon$-caprolactone) as measured using the ELISA technique (see Examples). The tTG was immobilised onto the surface for 1 hour at room temperature (see section 2.4.3. for details). Data represent mean values +/−S.D. (n=3).

The modified ELISA technique also demonstrated the binding of tTG to fibronectin coated PCL when tTG was immobilised by either evaporation overnight or by incubation for 1 h at room temperature (see FIGS. 6 and 7 respectively). FIGS. 6 and 7 clearly show that tTG can be immobilised to PCL using both methods. The maximum concentration of tTG that can be immobilised to the fibronectin coated PCL is approximately 30 µg/ml for both immobilisation techniques and the half maximum binding capacity is approximately 15 µg/ml.

The Activity of Tissue Transglutaminase, After Immobilisation onto the Biomaterial Surface (i) Quantitative Evaluation of the Activity of tTG on PCL when Immobilised in a 0.1M EDTA solution together with Fibronectin by Incubation at 4° C.

Figure 8:
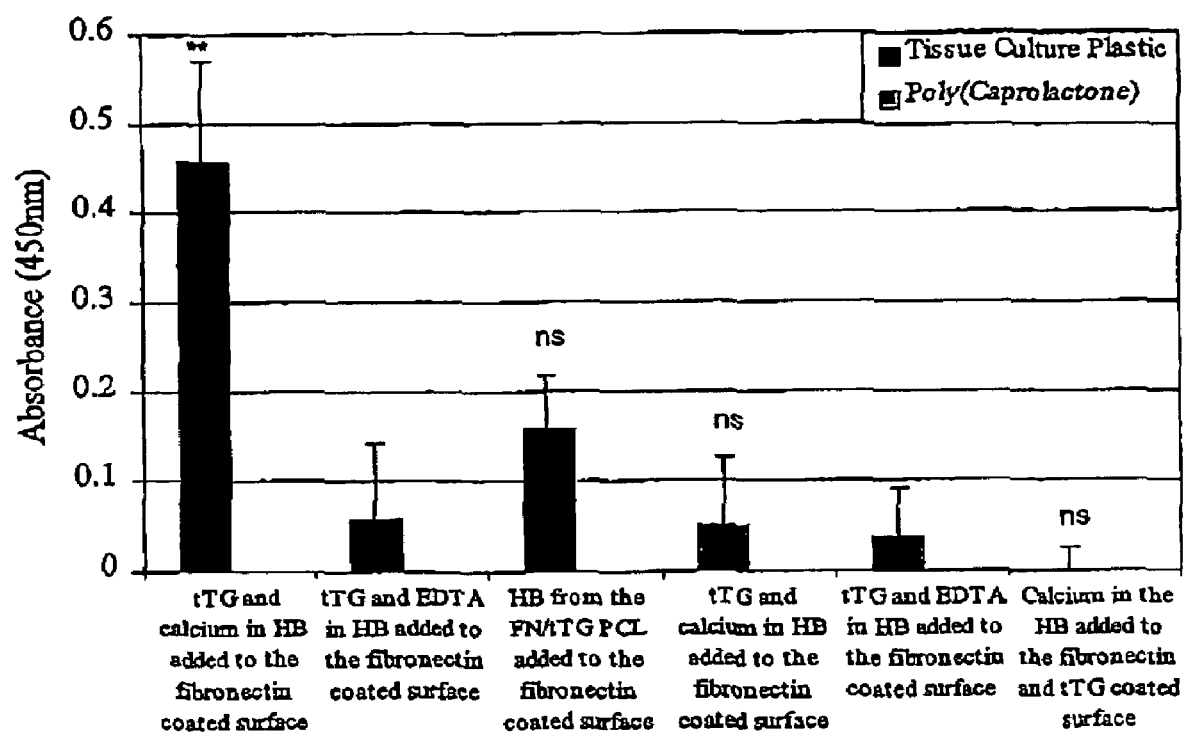
FIG. 8 shows the quantitative evaluation of the activity of tTG when immobilised onto PCL in solution with fibronectin (FN) overnight at 4° C., using the biotin-cadaverine incorporation (see Examples). A comparison with immobilisation on tissue culture plastic is also shown. HB equals buffer containing 5 mN Tris-HCl (pH 7.4), 0.25 M sucrose, 3.85 mM DTT. Calcium is added at a concentration of 5 mM and EDTA at a concentration of 5 mM. Data represent mean values +/−S.D. (n=3). Statistical analysis using one way analysis of variance (Anova) was performed on the data (**=P<0.01 and ns=not significantly different).

The activity of tTG on the PCL surface was evaluated using the biotin-cadaverine incorporation assay (see above). 15 µg/ml of fibronectin and 10 µg/ml tTG were immobilised onto the PCL ice by incubation together in a 0.1M EDTA solution overnight at 4° C. The data in FIG. 8 show that tTG is not active on the PCL surface or in the homogenising buffer removed from the same surface. This suggests that either fibronectin was not immobilised onto the PCL using ibis method (which needs to be confirmed using the ELISA technique) or the fibronectin adsorbed to the PCL was in a configuration unfavourable for tTG cross-linking. The positive control for PCL showed no significant tTG activity either, which again suggests that fibronectin is not present on the surface or is inaccessible for tTG cross-linking due to its unfavourable configuration. Another alternative would be that tTG did not bind to the fibronectin and was in an inactive form hence no activity was seen in the homogenising buffer either.

In further experiments the fibronectin and tTG concentrations were increased. It was also thought that 0.1M EDTA solution was too high a concentration for tTG binding as EDTA at this concentration might interfere with the tTG binding site on fibronectin molecule. Five mM EDTA was used in the preceding experiments (which is commonly used in the biotin cadaverine incorporation assay because it is high enough to inhibit tTG activity and yet low enough to allow the tTG to bind to the fibronectin).

(ii) Quantitative Evaluation of the Activity of tTG on Fibronectin-coated PCL When Immobilised by Evaporation in 5 mM EDTA.

Figure 9:
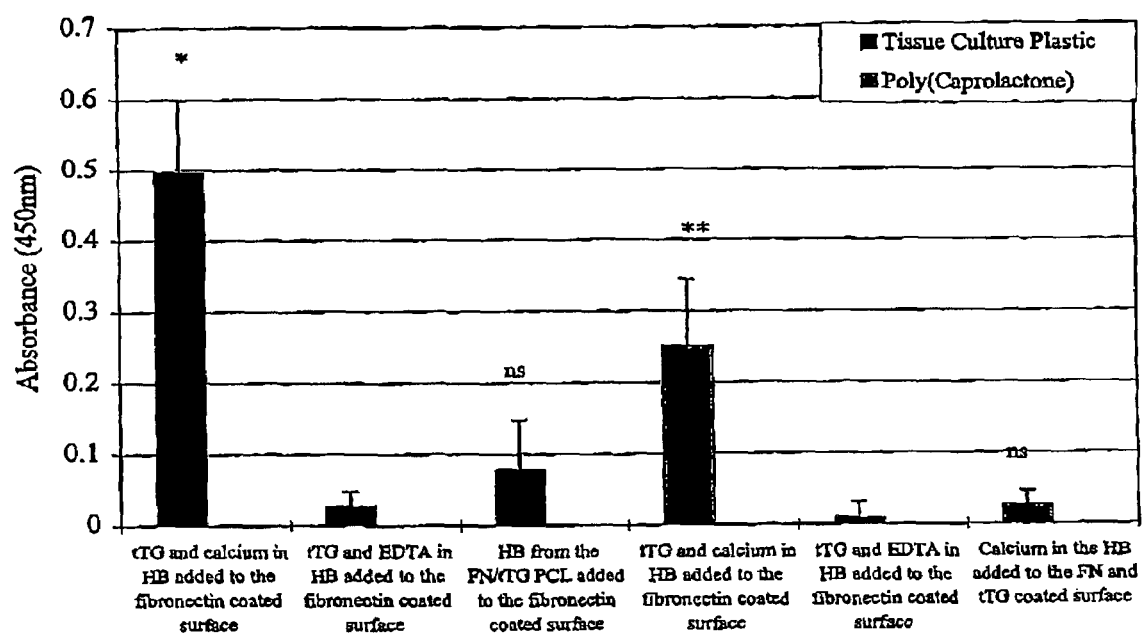
FIG. 9 shows the quantitative evaluation of the activity of tTG when immobilised onto fibronectin coated PCL by evaporation, using the biotin-cadaverine assay (see Examples). A comparison with immobilisation on tissue culture plastic is also shown. Data represent mean values +/−S.D. (n=3). Statistical analysis using one way analysis of variance (Anova) was performed on the data (**=P<0.01 and ns=not significantly different).

The activity of tTG on the PCL surface was evaluated using the biotin-cadaverine incorporation assay (see above). The tTG was immobilised onto the PCL by initially coating the surface with 30 µg/ml fibronectin by evaporation. A 5 mM solution of 20 µg/ml tTG was then added to the PCL in the same way (see above for details). The data in FIG. 9 show that the evaporation method allows the fibronectin to be immobilised onto the PCL in a configuration that is favourable for tTG cross-linking (see PCL-positive control, which shows that addition of tTG gives rise to biotin cadaverine incorporation on the fibronectin coated PCL surface. The presence of, fibronectin on the PCL surface when immobilised by this method was also confirmed by the ELISA assay (see FIG. 5). FIG. 9 also illustrates that the immobilised tTG is not active on the PCL when it is immobilised by evaporation overnight even though the ELISA results show that it is present on the surface (see FIG. 6). There was no significant tTG activity in the homogenising buffer which was removed from the fibronectin/tTG PCL surface, which also confirms that the tTG is present on the surface of the polymer.

Figure 10:
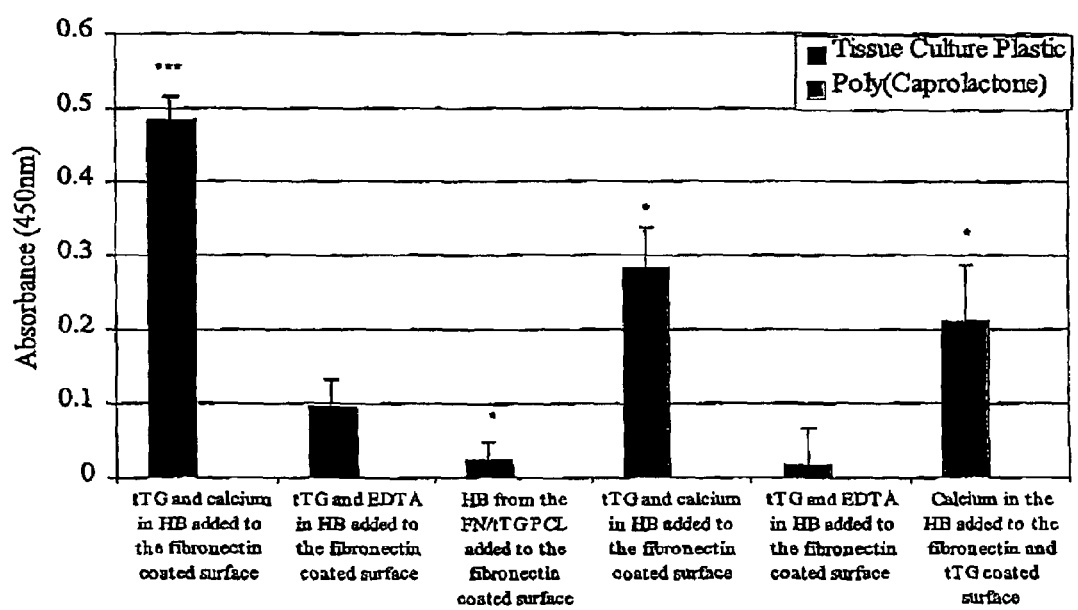
FIG. 10 shows the quantitative evaluation of the activity of tTG when immobilised onto fibronectin coated PCL by incubation at room temperature for one hour, using the biotin-cadaverine assay (see Examples). Data represent mean values +/−S.D. (n=3). Statistical analysis using one way analysis of variance (Anova) was performed on the data (*=P<0.001, =P<0.01, *=P<0.05 and ns=not significantly different).
Figure 11:
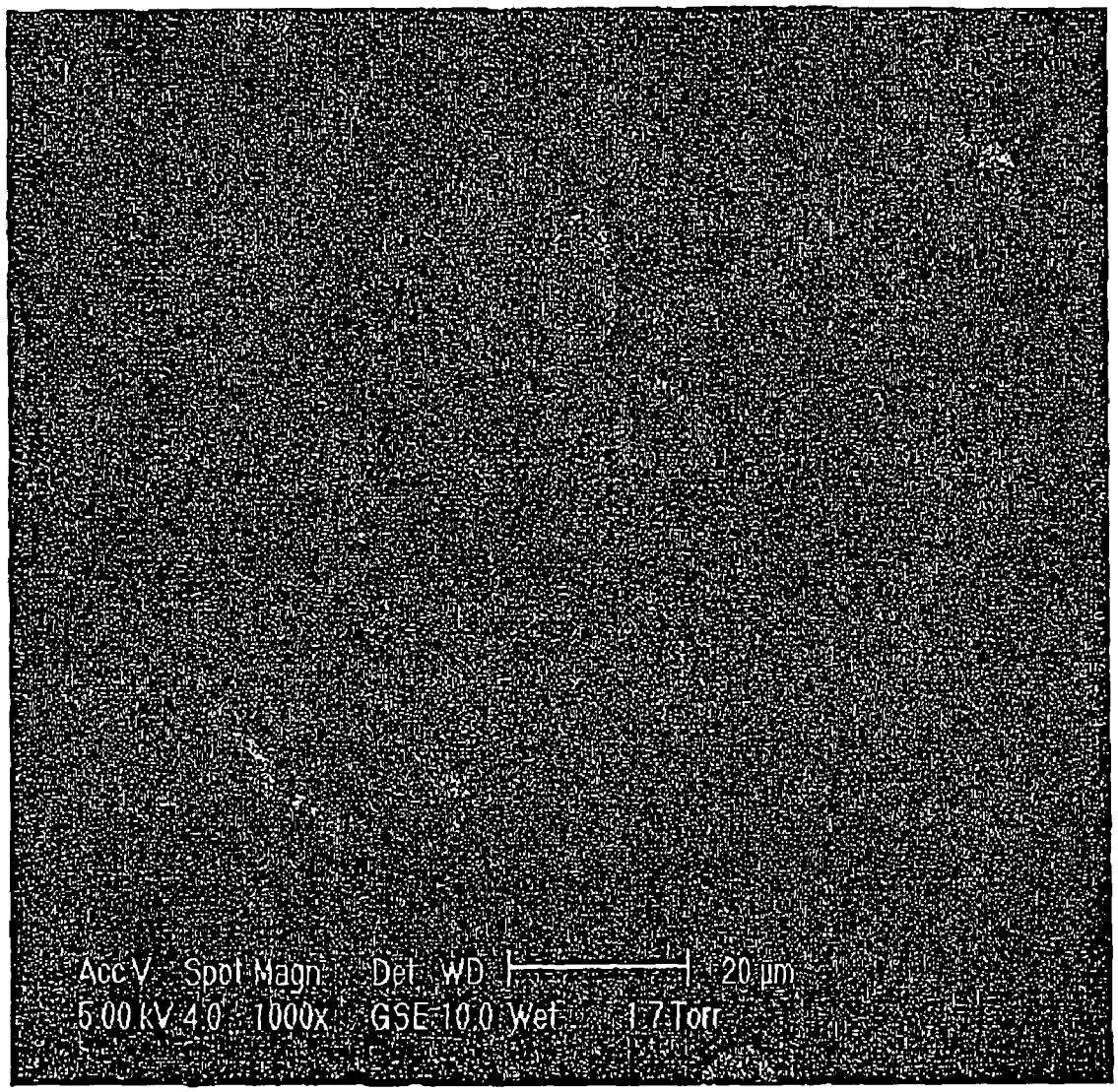
FIG. 11 shows a micrograph of human osteoblast cells on PCL in serum free medium, 30 minutes after cell seeding (viewed using E.S.E.M.). The cells are all rounded in morphology on the biomaterial surface.
Figure 12:
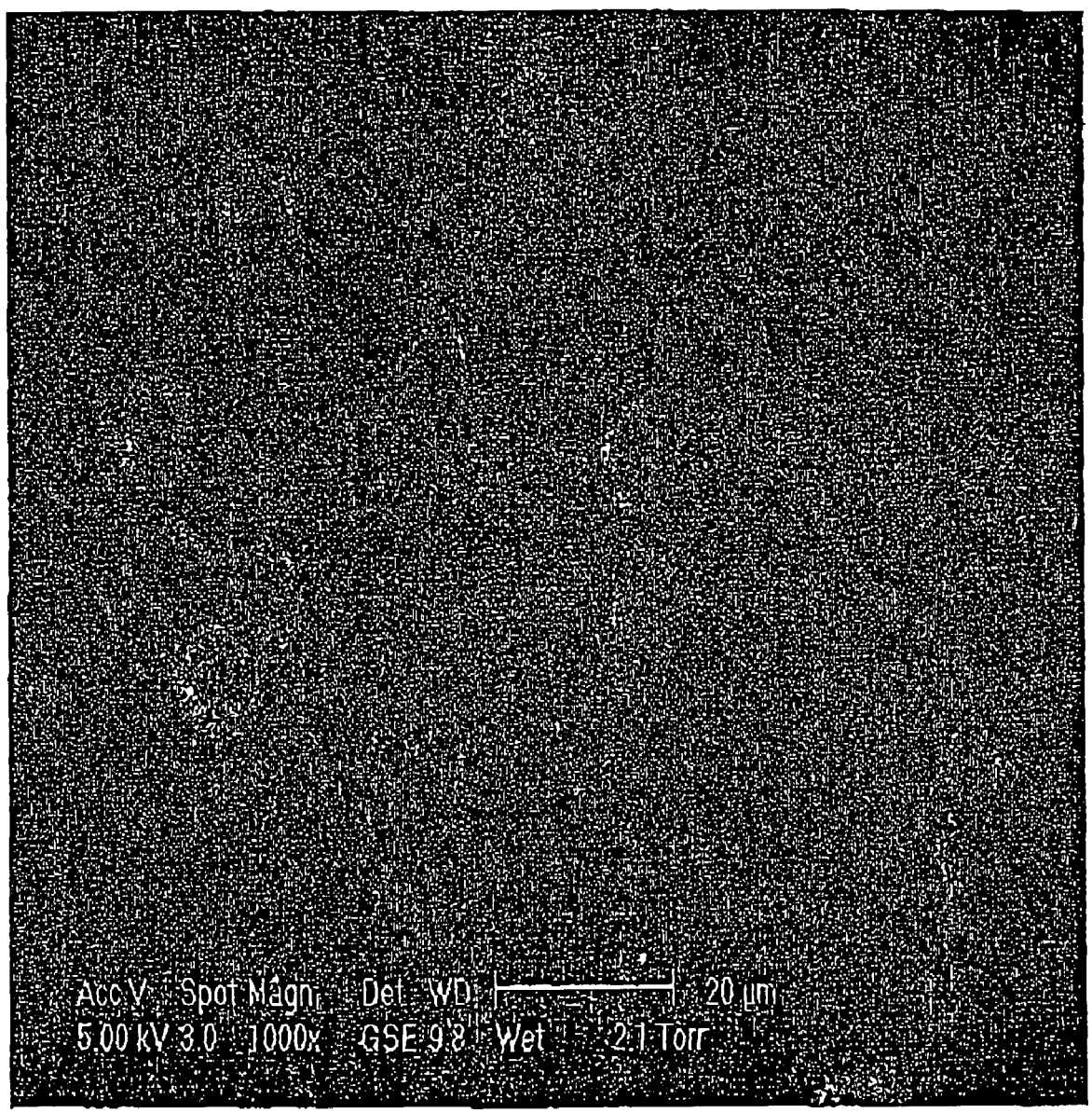
FIG. 12 shows a micrograph of human osteoblast cells in serum free medium on PCL coated with fibronectin, 30 minutes after cell seeding (viewed using E.S.E.M.). The cells have attached to the biomaterial and some cells have started to spread.
Figure 13:
FIG. 13 shows a micrograph of human osteoblast cells in serum free medium on PCL coated with fibronectin and tissue transglutaminase, 30 minutes after cell seeding (viewed using he E.S.E.M.). The cells have attached and the majority are well spread having a flat morphology.
Figure 14:
FIG. 14 shows a micrograph of human osteoblast cells in serum conning medium on tissue culture plastic, 30 minutes after cell seeding (viewed using E.S.E.M.). The cells have attached and have started to spread slightly.
Figure 15:
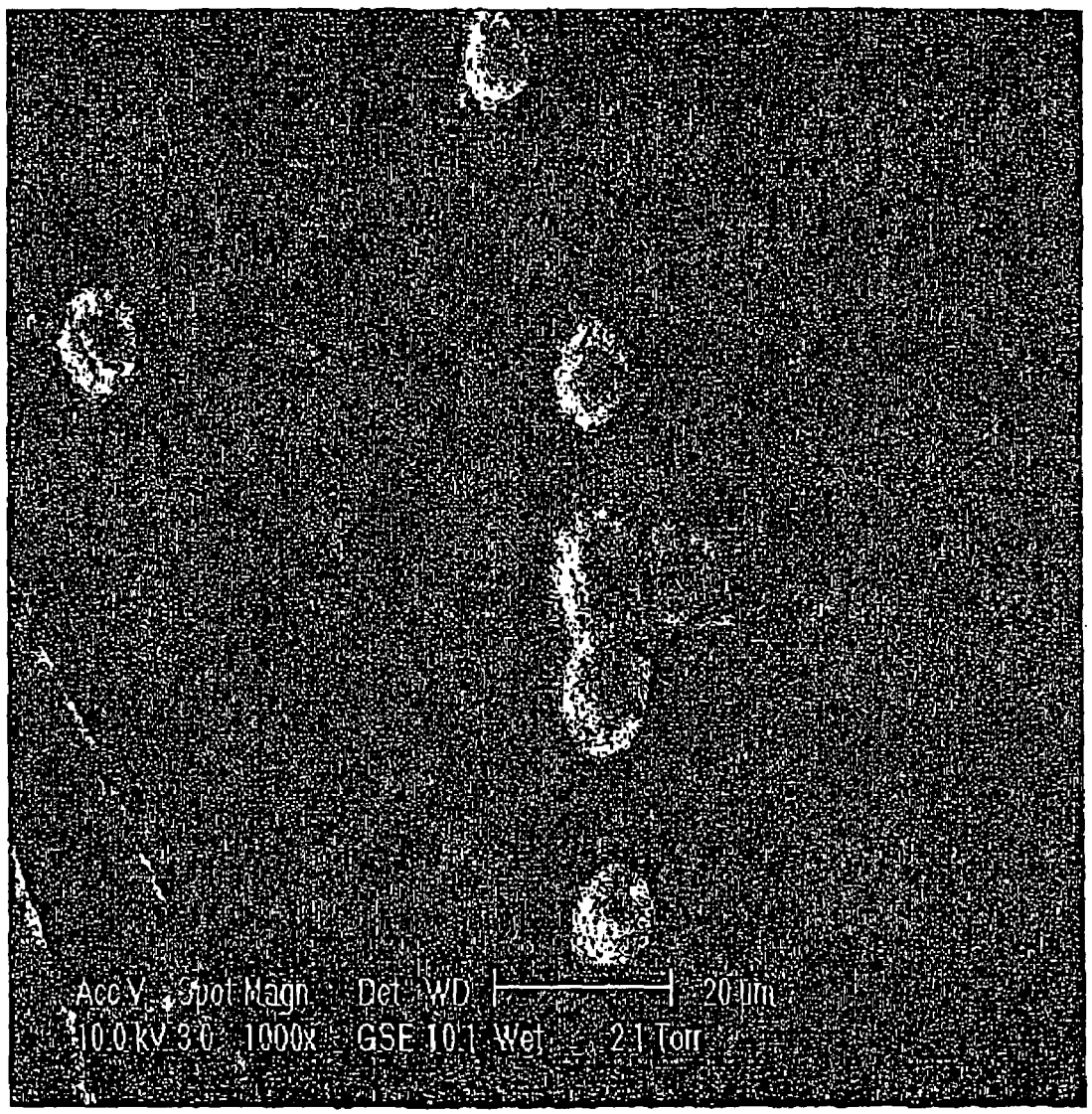
FIG. 15 shows a micrograph of human osteoblast cells on PCL in serum free medium, 60 minutes after cell seeding (viewed ling E.S.E.M.). The cells have attached to the PCL are starting to spread slightly.
Figure 16:
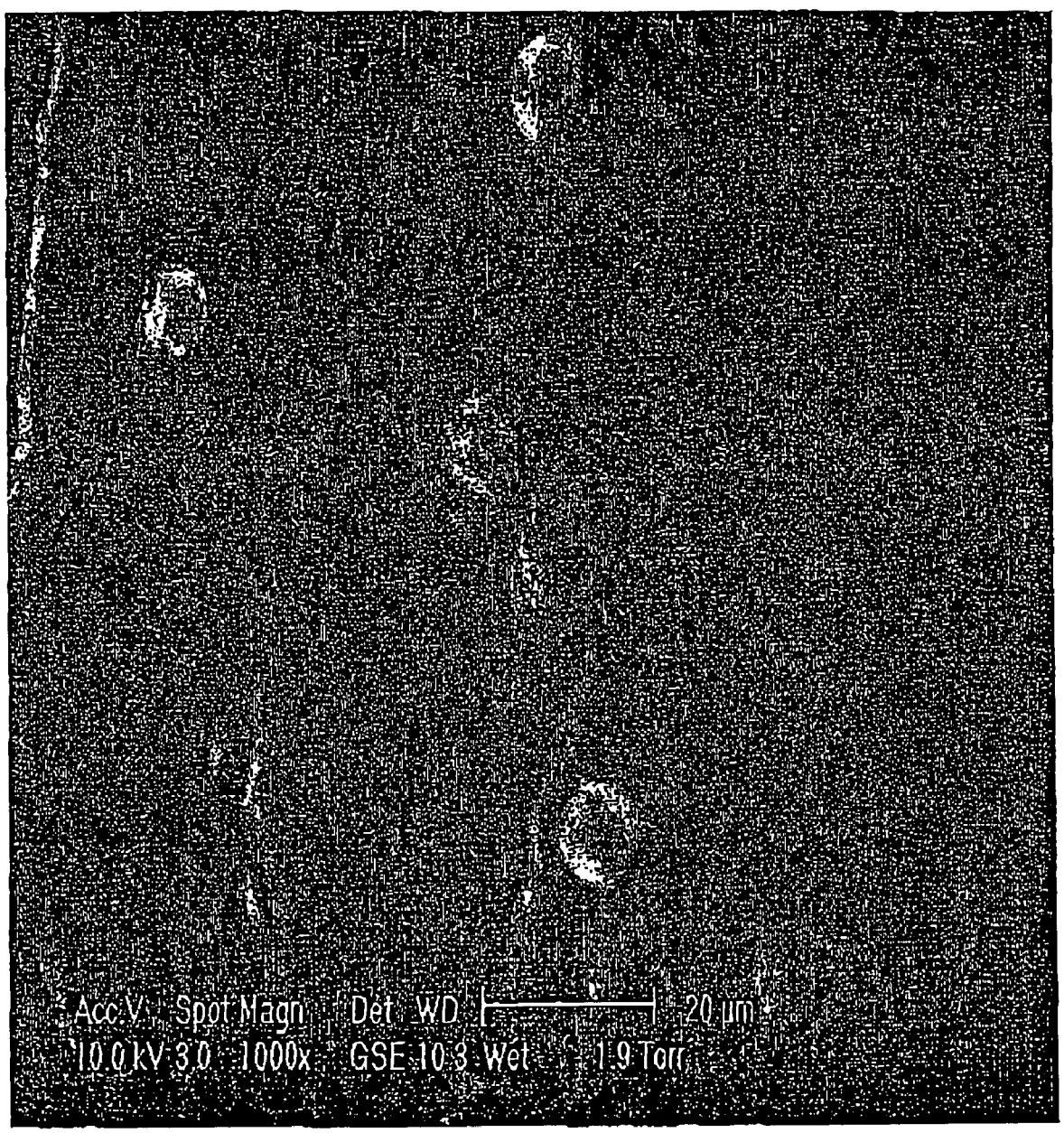
FIG. 16 shows a micrograph of human osteoblast cells in serum free medium on PCL coated with fibronectin, 60 minutes after cell seeding (viewed using E.S.E.M.). The results show a mixed morphology of rounded, slightly spread and flattened cells.
Figure 17:
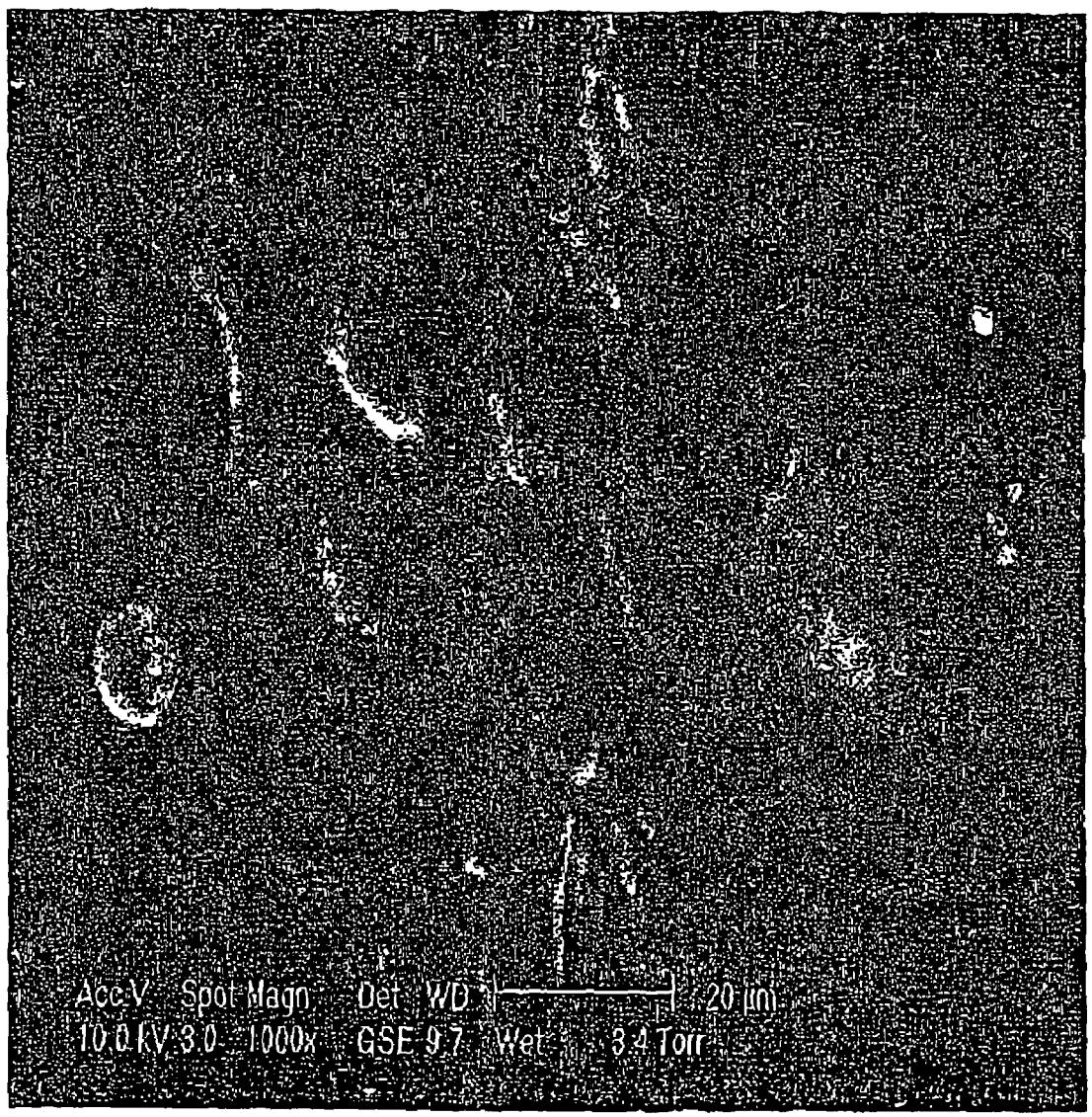
FIG. 17 shows a micrograph of human osteoblast cells in serum free medium on PCL coated with fibronectin and tissue transglutaminase, 60 minutes after cell seeding (viewed using E.S.E.M.). All the cells have spread and are flat in morphology on this particular surface.
Figure 18:
FIG. 18 shows a micrograph of human osteoblast cells in serum containing medium on tissue culture plastic, 60 minutes after cell seeding (viewed using E.S.E.M.). The cells have started to spread and some cells are flat in morphology.

(iii) Quantitative Evaluation of the Activity of tTG on Fibronectin-coated PCL When Immobilised by Incubation in 5 mM EDTA for One Hour at Room Temperature The activity of TG on the PCL surface was evaluated using the biotin-cadaverine incorporation assay (see section 2.7 for details). The tTG was immobilised onto the PCL by initially coating the surface with 30 µg/ml fibronectin by evaporation. A 5 mM solution of 20 µg/m tTG was then added to the PCL for 1 hour at room temperature (see above for details). FIGS. 9 and 10 both show that the evaporation method allows the fibronectin to be immobilised onto the biomaterial surface in a configuration that is favourable for tTG crossing (see PCL positive control, which shows that addition of tTG gives rise to biotin cadaverine incorporation on the fibronectin coated PCL. FIG. 10 also illustrates that immobilised tTG is present on the biomaterial surface and is active when immobilised for 1 h at room temperature. The ELISA technique (see FIG. 7) confirms that the tTG can be immobilised by this method. The homogenising buffer that was removed from the PCL that had previously been coated with fibronectin and tTG, showed no tTG activity when compared to the TCP negative control which confirms that tTG was immobilised to the PCL.

Human Osteoblast Cell Spreading on the Tissue Transglutaminase/Fibronectin Coated PCL:

HOB cells on tissue culture plastic (TCP) with and without 10% senum in the medium and PCL, PCL+fibronectin and PCL+fibronectin+tTG in serum free medium were cultured for 2 or 4 hours. After this, they were fixed and viewed using sa g electron microscopy (S.E.M.). The results clearly demonstrated that cell spreading occurred before 2 hours on the fibronectin/tTG coated PCL surface. Some distortion of the PCL surface occurred during the hydration step during S.E.M. sample preparation. The experiment was therefore repeated using smaller time points and viewed using environmental scanning electron microscopy (E.S.E.M.), which doesn't require a hydration step when preparing the sample. The samples were viewed in wet mode and the results are shown in FIGS. 11-21.

FIGS. 11-14 shows the degree of spreading of HOBs on various substrates at 30 minutes after cell seeding. The results clearly show that in 30 minutes the cells have attached and spread to the fibronectin/tTG coated PCL surface. Some of the cells are already at the late stages of cell spreading. The rate at which these cells spread was quicker than cells seeded on TCP in serum containing medium or on tie fibronectin coated PCL surface. It can be clearly seen that cells on PCL alone are rounded in morphology and show no signs of spreading at this particular time point.

After 1 hour incubation on the different surfaces, similar results were obtained (see FIGS. 15-18). The cells were spreading quicker on PCL coated with fibronectin+tTG than on fibronectin coated PCL or TCP. The cells on the fibronectin+tTG coated PCL, showed a more flattened morphology than seen at 30 minutes. Cells on PCL still remained rounded at this time point.

Figure 19:
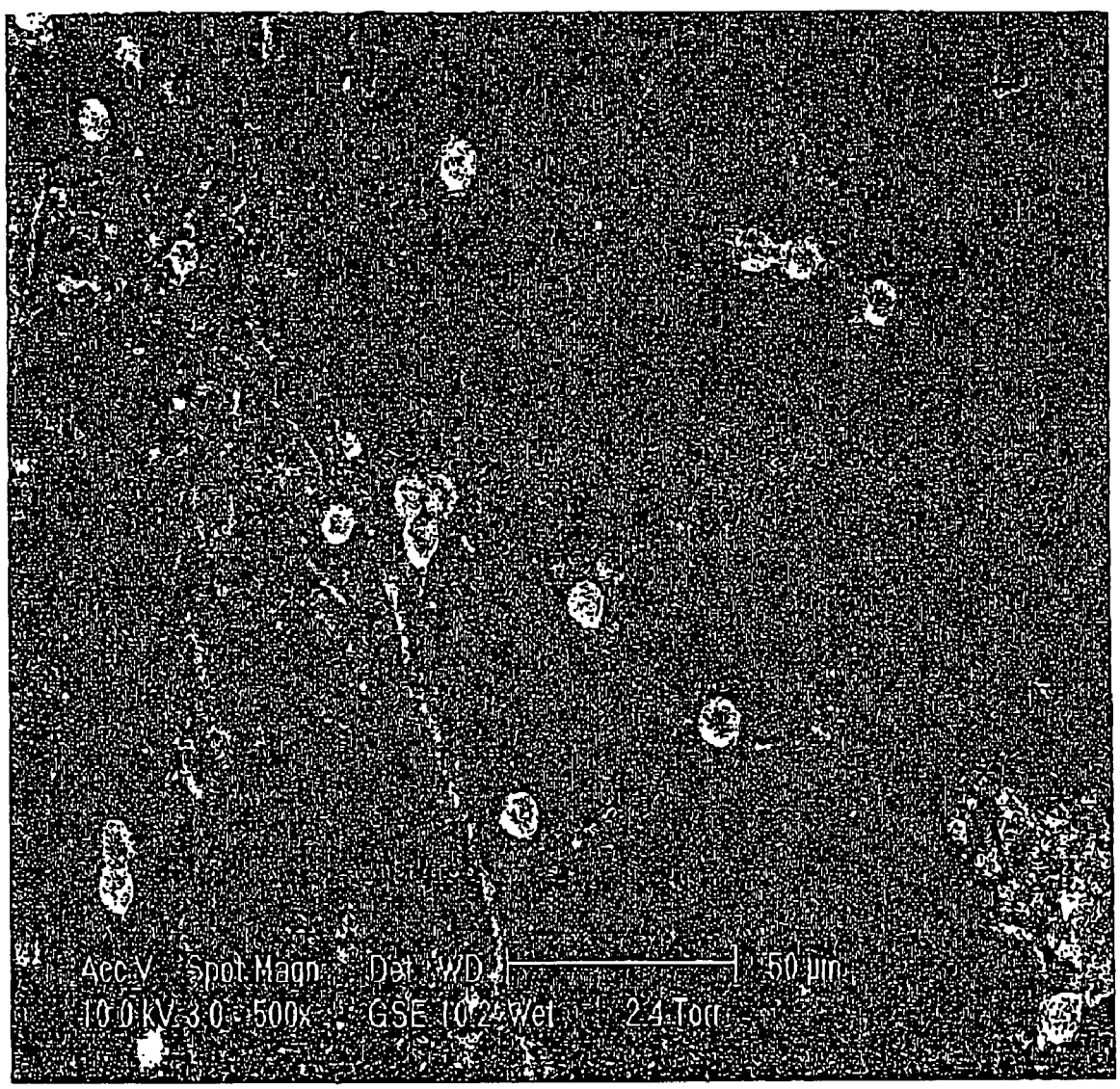
FIG. 19 shows a micrograph of human osteoblast cells on PCL in serum free medium, 3 hours after cell seeding (viewed using E.S.E.M.). The cells are all rounded in morphology. Some of the cells detached from the surface.
Figure 20:
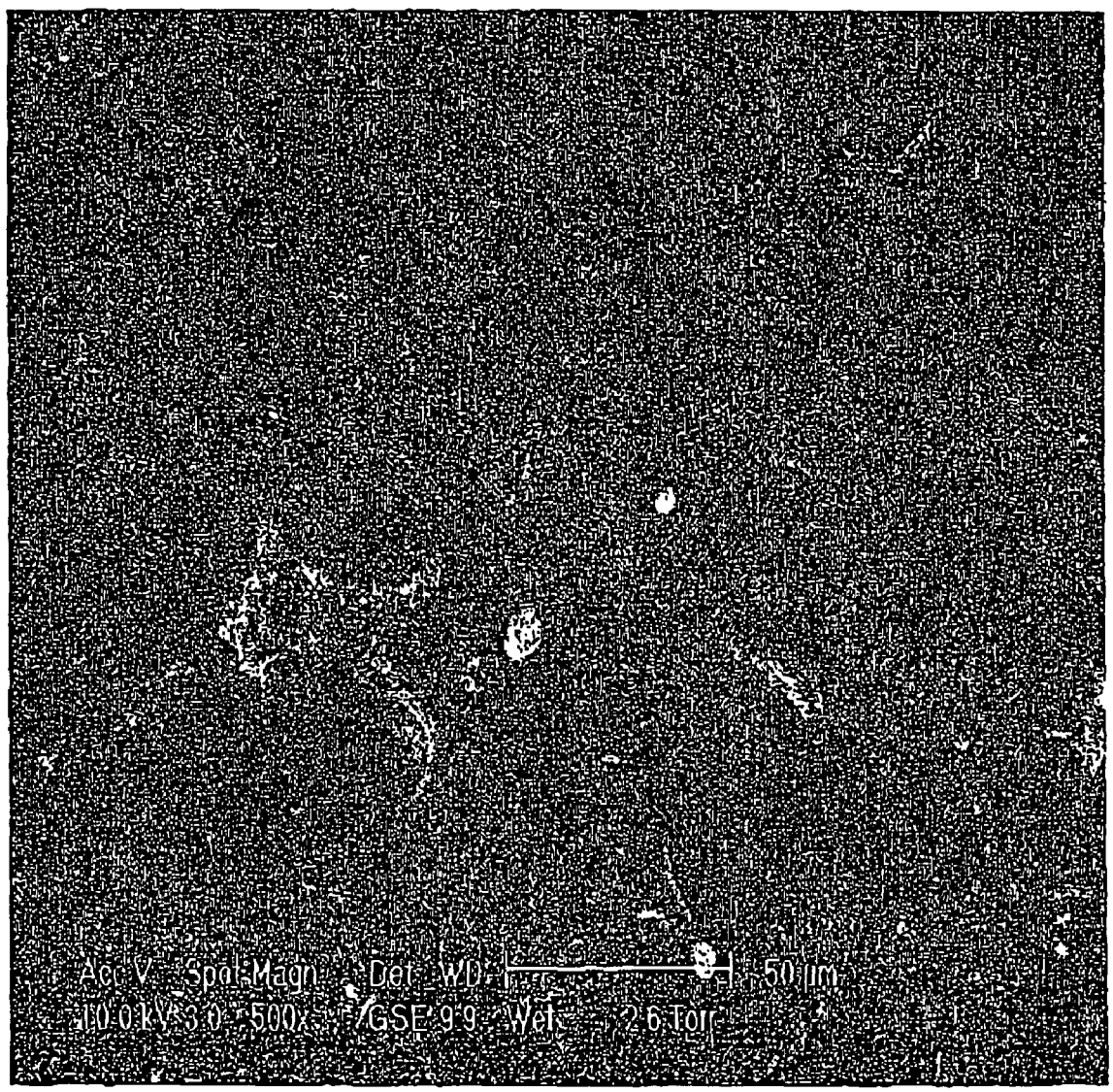
FIG. 20 shows a micrograph of human osteoblast cells in serum free medium on PCL coated with fibronectin, 3 hours after cell seeding (viewed using E.S.E.M.). The cells are all flat in morphology and form a monolayer over the surface of the biomaterial.
Figure 21:
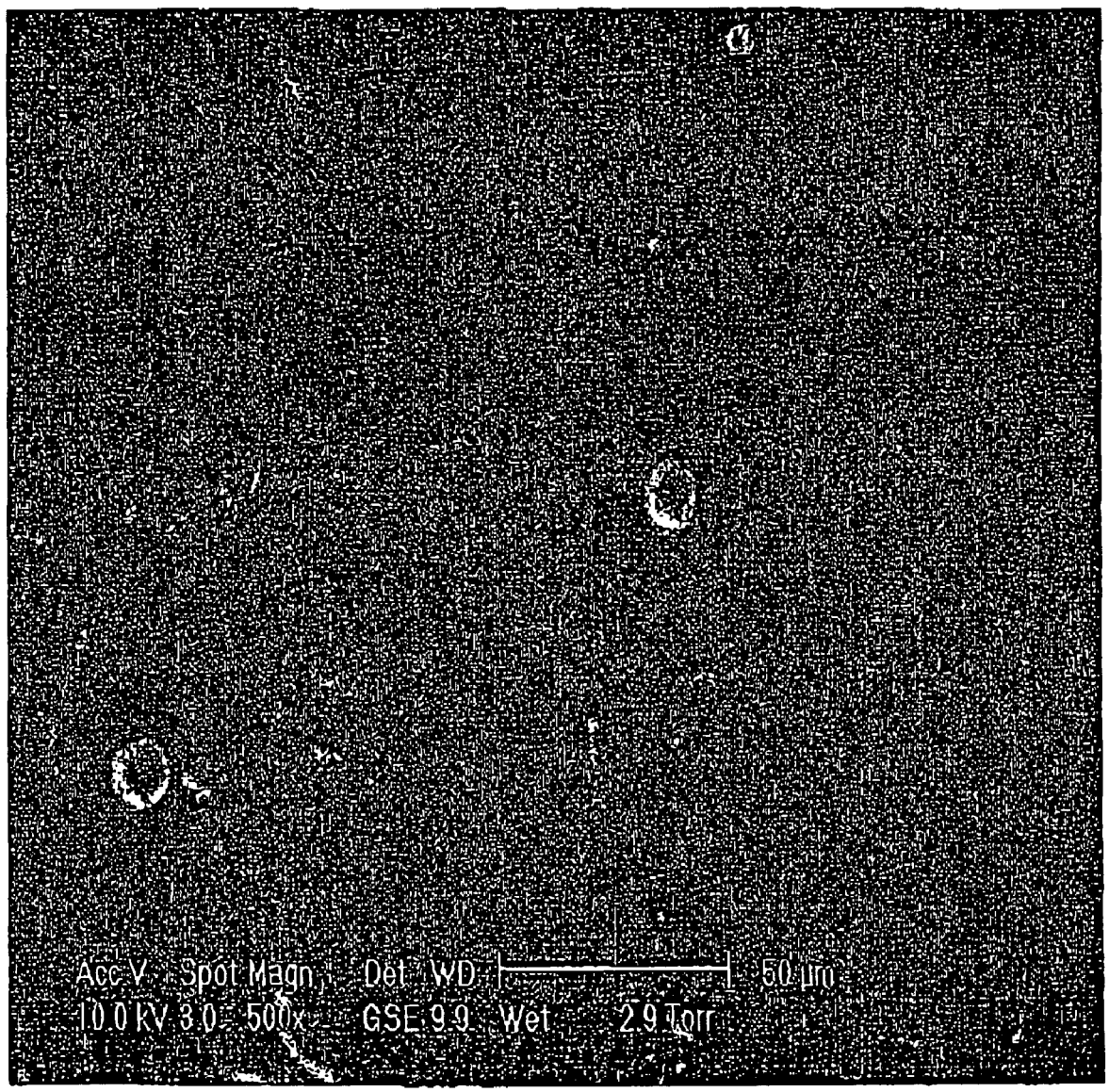
FIG. 21 shows a micrograph of human osteoblast cells in serum free medium on PCL coated with fibronectin and tissue transglutaminase, 3 hours after cell seeding (viewed using E.S.E.M.). The cells are all flat in morphology, forming a complete monolayer on the surface of this biomaterial.

FIGS. 19-21 show the degree of spreading 3 hours after seeding the HOB cells in serum free medium. The cells clearly remained rounded in morphology on the PCL. A lot of cells had detached from the biomaterial surface illustrating that HOB cells require adhesion proteins to spread on PCL. However, after 3 hours on the PCL+fibronectin and PCL+fibronectin+tTG surfaces the cells were flat in morphology and had formed a monolayer.

Figure 22:
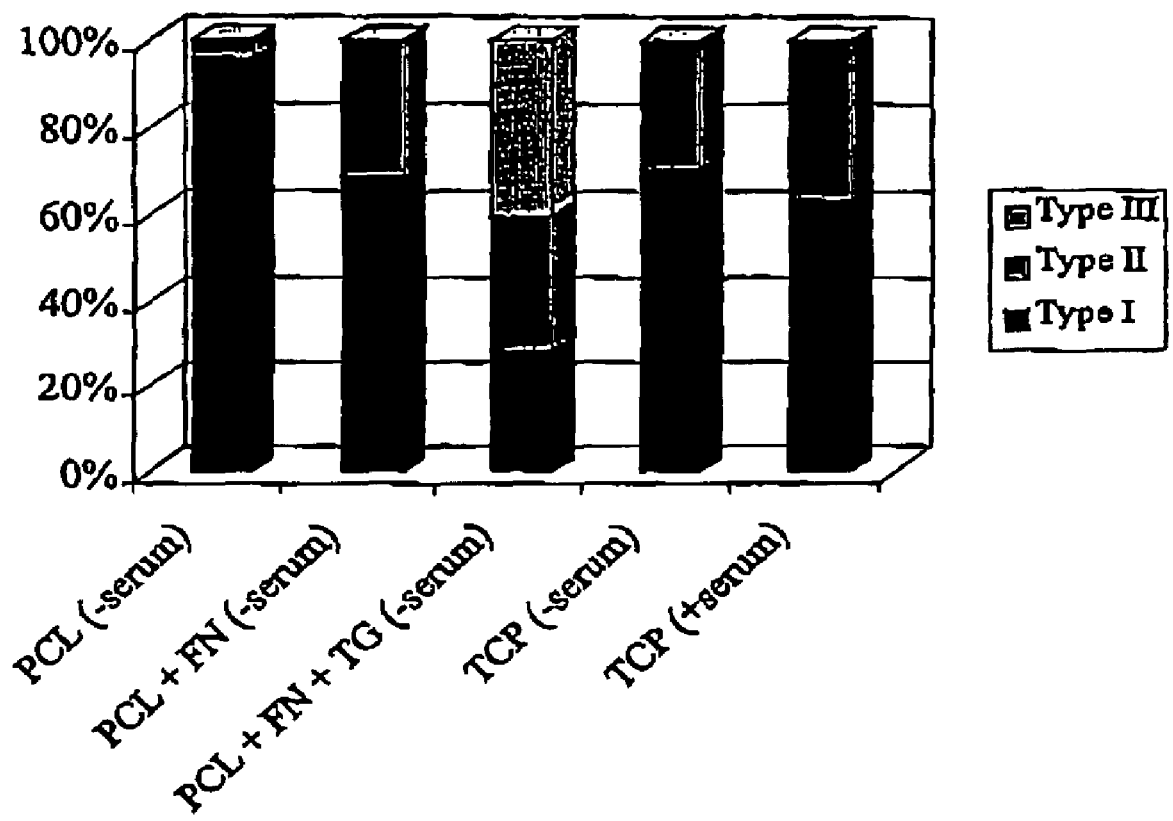
FIG. 22 shows HOB cell spreading on Poly(ε-caprolactone) (PCL) when coated with either fibronectin(FN) or fibronectin+tissue transglutaminase (N+tTG) 30 minutes after cell seeding. The cells were scored type I-III (type I being cells that have just attached and type III being cells in the late stage of spreading). These results were all compared to tissue culture plastic (TCP) with (+) and without (−) serum in the medium which were used as the positive and negative controls respectively.
Figure 23:
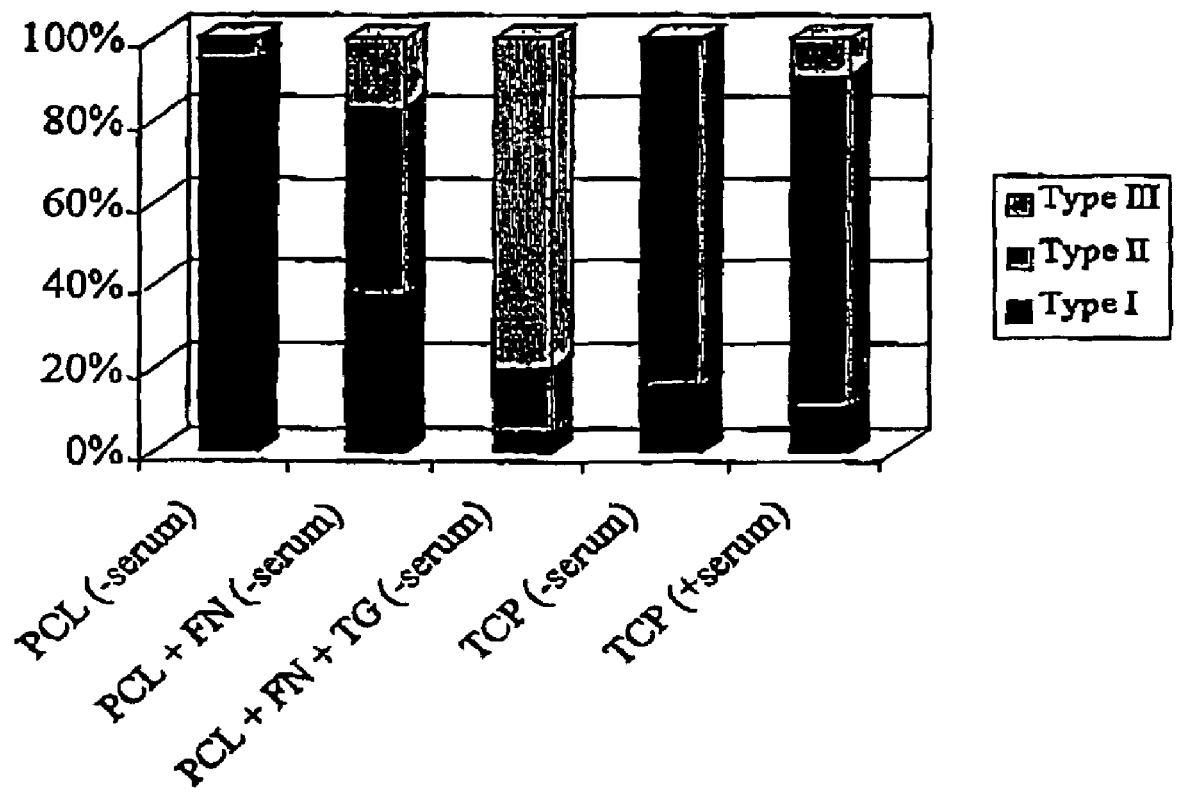
FIG. 23 shows human osteoblast cell spreading on Poly(ε-caprolactone) (PCL) when coated with either fibronectin(PN) or fibronectin+tissue transglutaminase (FN+tTG) 60 minutes after cell seeding. The cells were scored type I-III (type I being cells that have just attached and type III being cells in the late stage of spreading). These results were all compared to tissue culture plastic (TCP) with (+) and without (−) serum in the medium which were used as the positive and negative controls respectively.

FIGS. 22 and 23 show graphical data to summarise the effects tTG has on HOB cell spreading after 30 and 60 minutes (as viewed using E.S.E.M.). The degree of cell spreading was scored as type I-III. Type I was classed as cells that have attached to the surface but remain rounded in morphology. Type II cells are classed as cells that have attached to the surface and have started to spread. Type III cells are classed as those which have attached and spread out flat on the surface (late stage of spreading).

It can therefore be concluded from FIGS. 16-23 that HOB cells respond immediately to the tTG on the PCL surface, which subsequently causes earlier cell spreading. This surface is far more preferential to PCL alone or PCL coated with fibronectin.

Figure 24:
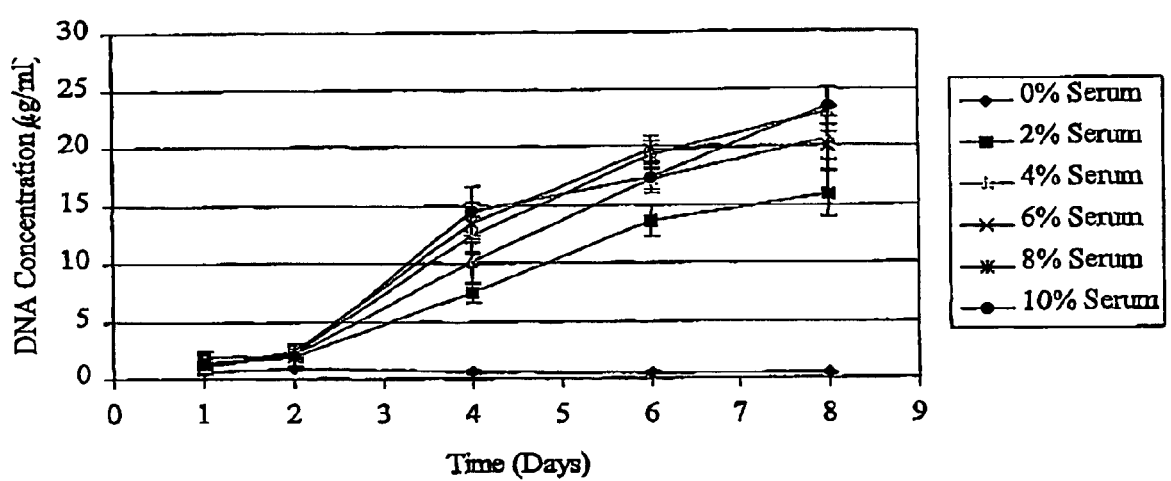
FIG. 24 shows the proliferation of HOBs on tissue culture plastic over 8 days, using various amounts of foetal calf serum in the medium. Cell numbers were analysed by measurement of total DNA using the method as described in section 2.9.1.1. The data represent mean values +/−S.D. (n=4). The results were statistically analysed using the t test.

Human Osteoblast Cell Differentiation on the Tissue Transglutaminase/Fibronectin-coated PCL Initially the minimum serum content of medium required for HOB cells to proliferate on TCP was investigated. The intention was to allow minimal interference of serum proteins with tTG when investigating its role in the differentiation of HOB cells when coated on PCL. FIG. 24 clearly shows that HOB cells cannot proliferate in serum free medium on TCP.

They can proliferate with as little as 2% serum im the medium. However the rate of proliferation is significantly slower than that of cells in the medium with a serum content of 4% or more.

Figure 25:
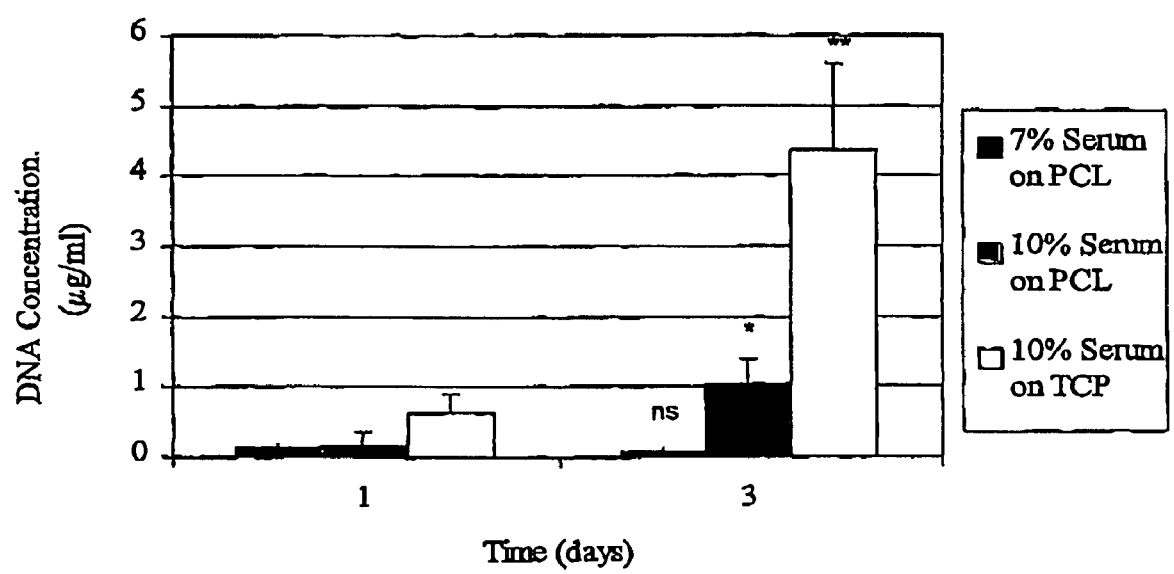
FIG. 25 shows the proliferation of human osteoblast cells on PCL in DMEM containing different amounts of foetal calf serum was investigated using the DNA Hoechst assay. The data represent mean values +/−S.D. (n=3), The results were analysed using one way analysis of variance (Anova) (**=P<0.01, *=P<0.05 and ns=not significantly different).

When the proliferation of HOB cells on PCL in varying amounts of serum containing medium was studied, it was found that a much higher serum content was required (see FIG. 25). There was no significant difference in DNA concentration between day 1 and day 3 when the cells were cultured in 7% serum cont medium. However, the DNA concentration was significantly higher between day 1 and day 3 for cells cultured in 10% serum containing medium. These results illustrate that the minimum content of serum in DMEM required for HOB cell proliferation on PCL, is 10%. At day 3, the number of cells on tissue culture plastic was significantly greater than the number of cells on PCL when both are cultured in 10% serum contating medium.

Discussion

The study of implant surface and biomaterial tissue interface reactions is essential for the continued improvement of implant performance. A review by Blitterwijk et al., (1991) discusses the importance of the reactions of cells at implant surfaces in determining the biocompatibility of the implant. Current research involves making bioactive materials, which will allow the integration of the material with the body. Many workers have introduced the concept of combining synthetic polymers with natural polymers to enhance biocompatibility.

In this study poly(ε-caprolactone) (PCL) was chosen and the natural polymer fibronectin was immobilised onto this surface. In a further attempt to stabilise and facilitate compatibility of the cell-biomaterial interface, the enzyme tissue transglutaminase (tTG) was also immobilised onto the fibronectin coated PCL surface. This enzyme catalyses the post-translational modification of proteins by forming inter and intramolecular ε(γ-glutamyl) lysine cross-links in inter- and intracellular proteins. The bonds that form are stable, covalent and resistant to chemical, enzymatic and physical disruption. The cross-linking of extracellular proteins is thought to enhance cellular responses such as cell attachment, spreading and differentiation at the biomaterial interface. However tTg may act as a receptor adhesive protein without protein crosslinking via its interaction with the $B_1$ and $B_3$ integrins (See Gaudry et al., 1999, *Exp. Cell. Res.* 252, 104-113; Akimov et al., 2000, *J. Cell. Biol.* 148, 825-838).

Jurgensen et al., (1997) showed that tTG could be a new biological 'glue' for cartilage-cartilage interfaces. Tissue TG has 62% greater adhesive strength than that of Tissucol, a commercially available fibrin-glue preparation Jones et al., (1997) showed that human endothelial cells transfected with anti-sense tTG, showed a decrease in cell adhesion and spreading. The theory of tTG being involved in cell attachment is also supported by the findings of Gentile et al., (1992) using Balb-c 3T3 fibroblasts, Borge et al., (1996) using chondrocytes and Verderio et al., (1998) using Swiss 3T3 Fibroblasts.

In the present study, three different methods were used to try and immobilise fibronectin and tTG. All methods were based on the theory that tTG would bind to the immobilised fibronectin on the PCL, because fibronectin has a tTG binding site (Jeong et al., 1995). This binding has been shown to be linked with the first 7 residues at the N terminal domain of tTG. However, reduction and alkylation of fibronectin, destroys its ability to associate with the tTG, suggesting that some features of its tertiary structure are necessary for the binding of the enzyme.

The tTG was immobilised onto the fibronectin coated PCL surface in either 0.1 M or 5 mM EDTA to prevent tTG cross-linking occurring before the biotin-cadaverine experiment was performed. It was hoped that this would not affect the binding properties of the enzyme. Jeong et al., (1995) showed that binding occurs in the absence of $Ca^{2+}$ and that the alteration in the conformation of the enzyme is not essential for the formation of the fibronectin-tTG complex.

The three methods of immobilising tTG to PCL were, a) adding fibronectin and tTG in solution overnight at 4° C., b) immobilising fibronectin onto the surface by evaporation and then immobilising tTG onto the surface by evaporation, c) immobilising fibronectin onto the surface by evaporation and then adding tTG and leaving it for 1 h at room temperature.

The ELISA techniques demonstrated the presence of fibronectin on PCL when immobilised by evaporation and also demonstrated the presence of tTG on fibronectin coated PCL when immobilised by either evaporation overnight or by incubation for 1 h at room temperature.

The activity of tTG on the PCL surface was evaluated using the biotin-cadaverine incorporation assay. It was found that tTG was not active on the surface of PCL when immobilised in solution together with fibronectin. An explanation for this would be that fibronectin is inaccessible for tTG cross-linking due to its unfavourable configuration or alternatively, the fibronectin did not bind to the PCL at 4° C. It was also found that tTG was not active on the fibronectin coated PCL surface when the tTG was immobilised by the evaporation method. An explanation for this would be that the evaporation method renders the tTG inactive as it was shown that under these circumstances tTG is present on the PCL surface (as demonstrated by the ELISA technique). When the tTG was immobilised by incubation for 1 h at room temperature however, it was found to be active on the surface.

Tissue transglutaminase is regulated by calcium and nucleotides (Smethurst and Griffin, 1996). They found that tTG was active at 100 μM calcium and when ATP or GTP were absent or in very low concentrations. In the cytoplasm of a resting energy-rich cell, the ATP levels may be as high as 8-11 mM and GTP levels between 50 and 300 μM, with a proportion of each being bound to cytosolic proteins, giving lower free nucleotide concentrations. In the resting state the free calcium is around 100-200 μM. Under these conditions their data suggest that tTG activity in the cytosol would be switched off. However, in DMEM (the medium that human osteoblast cells are cultured in) or in the in vivo situation there is >100 μM calcium, which is enough to activate the tTG on the biomaterial surface.

When the human osteoblast cells were seeded onto the fibronectin/tTG coated PCL surface, tTG had a profound effect on cell morphology (as viewed using E.S.E.M.). The results clearly demonstrated that cell spreading in serum free medium occurred 30 minutes after cell seeding unlike the cells on the PCL surface which remained rounded and unlike the cells on the PCL+fibronectin surface which had only just started to spread. The cells on the fibronectin/tTG coated surface spread quicker than cells seeded on tissue culture plastic in 10% serum containing medium (positive control).

After 1 hour incubation on the different surfaces, similar results were obtained and 3 hours after cell seeding the human osteoblast cells had formed a monolayer on PCL+fibronectin, PCL+fibronectin+tTG and on tissue culture plastic. The cells on PCL however, were still rounded in morphology and only a few cells were present indicating that some cells had probably detached during the hour.

It can therefore be concluded from the E.S.E.M. results, that human osteoblast cells immediately respond to the tTG on the PCL surface, which subsequently causes earlier cell spreading. This surface is far more preferential to PCL alone, PCL coated with just fibronectin and tissue culture plastic.

Cells initially attach to the biomaterial by physicochemical factors, i.e. charge, surface free energy or the water content of the biomaterial (Schamberger and Gardella, 1994) and then strongly adhere to ECM proteins, which have been deposited on the biomaterial surface. It is thought that initially the cells attach to the fibronectin coated PCL surface. Evidence then suggests that tTG cross-links the fibronectin with other cell surface bound proteins forming a stabilised extracellular matrix on the biomaterial face. Cross-linking of the surface bound proteins may also trigger the activation of integrins. The cell may also utilise the tTG as an adhesion protein in association with the β1 integrin in order for it to attach to the biomaterial surface. Gaudry et al., (1999) has shown that tTG co-localises with the β1 integrin and Akimov et al., 2000, *J. Cell. Biol.* 148, 825-8 has suggested that tTg may mediate the interaction between the B1 and B3 integrins and fibronectin.

The differentiation of human osteoblast cells on the tTG coated PCL surface was investigated. It was necessary to first establish the lowest amount of serum required in DMEM that will allow osteoblast proliferation. The results showed that cells can proliferate in as little as 2% serum containi medium on tissue culture plastic, however they require a minimum of 10% serum containing medium when cultured on PCL. The rate of proliferation is also slower on PCL than on tissue culture plastic.

The differentiation of cells on the TCP. PCL, PCL+FN and PCL+FN+tTG surfaces was measured 2 days after cell seeding using the alkaline phosphatase activity assay and was expressed as per μg DNA. The preliminary results indicate that tTG, does not have any detrimental effect on the alkaline phosphatase activity/differentiation of HOB cells on PCL when compared to PCL coated with fibronectin. However, this needs to be investigated at later time points. Kaartinen et al., (1999), however believes that the cross-linking of osteopontin (a major noncollagenous bone protein) by tTG increases its collagen binding properties. This leads us to believe that tTG may be a promoter of cell differentiation because it not only cross-links extracellular proteins but also helps in ECM molecule recruitment.

Poly(ε-caprolactone) coated with fibronectin and tissue transglutaminase is a bioactive biomaterial that enhances cell attachment, spreading and stabilises the extracellular matrix on the biomaterial surface making the human osteoblast-biomaterial interface stable. This biomaterial has potential applications in bone grafting where cells need to rapidly colonise the biomaterial in order to produce new bone. The PCL could also be re-enforced to give it the mechanical strength required for hip and knee prosthesis.

REFERENCES

Achyuthan, K. E. and Greenburg, C. S. (1987): Identification of a guanosine triphosphate-binding site on guinea pig liver tissue transglutaminase: Role of GTP and calcium ions modulating activity. *Journal of Biological Chemistry*, 262, 1901-1906.

Achyuthan, K. B., Goodell, R. J., Kennedye, J. R., Lee, K. N., Henley, A., Sliefer, J. R. and Birckbichler, P. J. (1995): Immunochemical Analysis of Human Plasma Fibronectin-Cytosolic Transglutaminase Interactions. *Journal of Immunological Methods*, 180, 69-79.

Aeschlimann, D., Wetterwald, A., Fleisch, H. and Paulsson, M. (1993): Expression of Tissue Transglutaminase in Skeletal Tissues Correlates With Events of Terminal Differentiation of Chondrocytes. *The Journal of Cell Biology*, 120 (6), 1462-1470.

Aeschimann, D. and Paulsson, M. (1994): Transglutaminases: Protein Cross-Linking Enzymes in Tissues and Body Fluids. *Thrombosis and Haemostasis*, 71(4), 402-425.

Aeschimann, D., Kaupp, O. and Paulsson, M. (1995); Transglutaminase-Catalysed Matrix Cross-Linking in Differentiating Cartilage: Identification of Osteonectin as a Major Glutaminyl Substrate. *The Journal of Cell Biology*, 129(3), 881-892.

Aeschimann, D., Mosher, D. and Paulsson, M. (1996): Tissue transglutaminase and Factor XIII in Cartilage and Bone Remodeling. *Seminars in Thrombosis and Hemostasis*, 22(5), 437-443.

Akimov, S. S., Krylov, D., Fleischman, L. F. and Belkin, A. M. (2000). Tissue transglutaminase is an integrin-binding adhesion co-receptor for fibronectin. *J. Cell Biol.* 148, 825-838.

Ali, S. A. M., Doherty, P. J. and Williams D. F. (1992): In Vitro Hydroxy Radical Degradation of Poly(Caprolactone). *Biomaterial Tissue Interfaces*, 10, 399-403.

Ali, S. A. M., Zhong, S. P., Doherty, P. J. and Williams, D. F. (1993): Mechanisms of Polymer Degradation in Implantable Devices, I. Poly(Caprolactone). *Biomaterials,* 14(9), 648-656.

Ali, S. A. M., Doherty, P. J. and Williams D. F. (1994): Molecular Biointeractions of Biomedical Polymers with Extracellular Exudate and Inflammatory Cells and their Effects on the Biocompatibility, In Vivo. *Biomaterals,* 15(10), 779-785.

Barsigian, C., Stern, A. M. and Martinez, J. (1991): Tissue Type II) Transglutaminase Covalently Incorporates Itself, Fibrinogen or Fibronectin into High Molecular Weight Complexes on the Extracellular Surface of Isolated Hepatocytes. *The Journal of Biological Chemistry,* 266(33), 22501-22509.

Bei, J., Wang, Z. and Wang, S. (1995): Poly(caprolactone)-Poly(ethylene glycol) Block Copolymer III, Drag Release Behaviour. *Chinese Journal of Polymer Science,* 13(2), 154-161.

Bendixen, E., Borth, W. and Harpel, P. C. (1993): Transglutaminases Catalyse Cross-Linking of Plasminogen to Fibronectin and Human Endothelial Cells. *The Journal of Biological Chemistry,* 268(29), 21962-21967.

Beninati, S., Senger, D. R., Cordella-Miele, B., Mukherjee, A. B., Chackalaparmpil, I., Shanmugam, V., Singh, K. and Mukherjee, B. B., 1994: Osteopontin: Its Transglutaminase-Catalysed Posttranslational Modifications and Cross-Linking to Fibronectin. *Journal of Biochemistry,* 115, 675-682.

Blitterswijk, C. A., Bakker, D., Hesseling, S. C. and Koerten, H. K. (1991): Reactions of Cells at Implant Surfaces. *Biomaterial,* 12, 187-193.

Borge, L., Demignot, S. and Adolphe, M. (1996): Type II Transglutaminase Expression in Rabbit Articular Chondrocytes in Culture: Relation with Cell Differentiation, Cell Growth, Cell Adhesion and Cell Apoptosis. *Biochimica et Biophysca Acta,* 1312, 117-124.

Bowness, J. M., Tarr, A. H. and Wong, T. (1988): Increased Transglutaminase Activity During Skin Wound Healing in Rats. *Biochimica et Biophysica Acta,* 967, 234-240.

Cascone, M. G., DiSilvio, L., Sim, B. and Downes, S. (1994): Collagen and Hyaluronic Acid Based Polymeric Blends as Drug Delivery Systems for the Release of Physiological Concentrations of Growth Hormone. *Journal of Materials Science: Materials in Medicine,* 5, 770-774.

Cha, Y. and Pitt, C. G. (1990): The Biodegradability of Polyester Blends. *Biomaterials,* 11, 108-112.

Clarke, E. A. and Brugge, J. S. (1995): Integrins and Signal Transduction Pathways: the Road Taken. *Science,* 286, 233-239.

Coombes and Meike (1994): Resorbable Synthetic Polymers as Replacements for Bone Graft. *Clinical Materials,* 17, 35-67.

Daniels, A. U., Chang, M. K. O. and Andriano, K. P. (1990): Mechanical Properties of Biodegradable Polymers and Composites Proposed for Internal Fixation of Bone. *Journal of Applied Biomaterials,* 1, 57-78.

Demignot, S., Borge, L. and Adolphe, M. 1995: Transglutaminase activity in rabbit articular chondrocytes in culture. *Biochimica et Biophysica Acta,* 1266, 163-170.

Dzamba, B. J., Bultmann, H., Akiyama, S. K. and Peters, D. M. (1994): Substrate Specific Binding of the Amino Terminus of Fibronactin to an Integrin Complex in Focal Adhesions. *Journal of Biological Chemistry,* 269, 19646-19652.

Ellis, D. L. and Yannis, I. V. (1996): Recent Advances in Tissue Synthesis In Vivo by use of Collagen-Glycosiniglycan Copolymers. *Biomaterials,* 17, 291-299.

Feng, X. D., Song, C. X. and Chen, W. Y. (1983): Synthesis and Evaluation of Biodegradable Block Copolymers of □-Caprolactone and DL-Lactide. *Journal of Polymer Science: Polymer Letters Edition,* 21, 593-600.

Fesus, L., Metsis, M. L., Muszbek, L. and Koteliansky, V. E. (1986): Transglutaminse-Sensitive Glutamine Residues of Human Plasma Fibronectin Revealed by Studying its Proteolytic Fragments. *European Journal of Biochemistry,* 154, 371-374.

Fraij, B. M. and Gonzales, R. A., 1997: Organisation and Structure of the Human Tissue Transglutaminase Gene. *Biochimica et Biophysica Acta,* 1345, 65-71.

Gaudry, C. A. (1998): Tissue Transglutaminase: A New Secretory Protein. PhD Thesis, The Nottingham Trent University.

Gaudry, C. A., Verderio, B., Jones, R. A., Smith, C. and Giffin, M. (1999): Tissue Transglutaminase is an Important Player at the Surface of Human Endothelial Cells: Evidence for its Externalisation and its Colocalisation with the $\alpha_1$ Integrin. *Experimental Cell Research,* 252, 104-113.

Gentile, V., Thomazy, V., Piacentini, M., Fesus, L. and Davies, P. J. A. (1992): Expression of Tissue Transglutaminase in Balb-C 3T3 Fibroblasts: Effects on Cellular Morphology and Adhesion. *The Journal of Cell Biology,* 119 (2), 463-474.

Giusti, P., Lazzeri, L., De Petris, S., Palla, M. and Cascone, M. G. (1994): Collagen-Based New Bioartificial Polymeric Materials. *Biomaterials,* 15(15), 1229-1233.

Greenberg, C. S., Birckbichler, P. J. and Rice, R. H. (1991): Transglutaminase: Multifunctional Crosslinking Bites that Stabilise Tissues. *FASEB,* 5, 3071-3077.

Groenen, P. J. T. A., Smulders, R. H. P. H., Peters, R. F. R. and Grootjans, J. J. 1994. The Amine-Donor Substrate Specificity Of Tissue-Type Transglutaminase: Influence Of Amino Acid Residues Flanking The Amine-Donor Lysine Residue. *European Journal of Biochemistry,* 220, 795-799.

Grootjans, J. J., Groenen, P. J. T. A. and de Jong, W. W. 1995. Substrate Requirements For Transglutaminases. *The American Society For Biochemistry and Molecular Biology,* 270(39), 22855-22858.

Gurav, N. and Downes, S. (1994): A Qualitative In Vitro Evaluation of the Degradable Materials Poly(caprolactone), Poly(hydroxybutyrate) and a Poly(hydroxybutyrate)-(hydroxyvalerate) Copolymer. *Journal of Materials Science: Materials in Medicine,* 5, 784-787.

Gurav, N., Kayser, M. V. and Downes S. (1996): In Vitro Biocompatibility Testing of Degradable Polymers. Fifth World Biomaterial Congress, May 29th-June 2nd, Toronto, Canada.

Heath, D. J. (2000): The stabilisation of the Extracellular Matrix on Biomaterial Surfaces, Thesis, University of Nottingham.

Hohenadl, C., Mann, K., Mayer, U., Timpl, R., Paulsson, M. and Aeschlimann, D., 1995: Two Adjacent N-Terminal Glutamines of BM-40 (Osteonectin, SPARC) Act as Amine Acceptor Sites in Transglutaminase—Catalysed Modification. *The Journal of Biological Chemistry,* 270 (40), 23415-23420.

Jeong, J- M., Murthy, S. N. P., Radek, J. T., and Lorand, L. (1995): The Fibronectin-Binding Domain of Transglutaminase. *The Journal of Biological Chemistry,* 270 (10), 5654-5658.

Jianzhong B. E. I., Zhifeng, W. and Shenguo, W. (1995): Poly(Caprolactone)-Poly(Ethylene Glycol) Block Copolymer III Drug Release Behavior. *Chinese Journal of Polymer Science,* 13(2), 154-161.

Jones, R. A., Nicholas, B., Mian, S., Davies, P. J. A. Griffin, M. (1997): Reduced Expression of Tissue Transglutaminase in a Human Endothelial Cell Line Leads to Changes in Cell Spreading, Cell Adhesion and Reduced Polymerisation of Fibronectin. *Journal of Cell Science,* 110, 2461-2472.

Juliano, R. L. and Haskill, S. (1993): Signal Transduction form the Extracellular Matrix. *Journal of Cell Biology,* 120, 577-585.

Jurgensen, K., Aeschlimann, D., Cavin, V., Genge, M. and Hunziker, B. B. (1997): A New Biological Glue for Cartilage-Cartilage Interfaces: Tissue Transglutaminases. *Journal of Bone and Joint Surgery,* 79(2), 185-193.

Kaartinen, M. T., Pirhonen, A, Linnala-Kankkunen, A. and Maenpa, P. -H. 1997: Transglutaminase-catalysed Crosslinking of Osteopontin Is Inhibited by Osteocalcin. *The Journal of Biological Chemistry,* 272(36), 22736-22741

Kaartinen, M. T., Pirhonen, A, Linnala-Kankkunen, A. and Maenpa, P. H. (1999): Cross-linking of Osteopontin by Tissue Transglutaminase Increases Its Collagen Binding Properties. *Journal of Biological Chemistry,* 274(3), 1729-1735.

Lemmouchi, Y., Schacht, E., Kageruka, P., De Deken, R., Diarra, B., Diall, O. and Geerts, S. (1998): Biodegradable Polyesters for Controlled Release of Trypanocidal Drugs: In Vitro and In Vivo Studies. *Biomaterials,* 19, 1827-1837.

LeMosy, E. K., Erickson, H. P., Beyer, W. F., Radek, J. T., Jeong, J., Murthy, P. S. N. and Lorand, L., 1992. Visualisation of Purified Fibronectin-Transglutaminase Complexes. *The Journal of Biological Chemistry,* 267(11), 7880-7885.

Lesort, M., Attanavanich, K., Zhang, J. and Johnson, G. V. W., 1998: Distinct Nuclear Localisation and Activity of Tissue Transglutaminase. *Journal of Biological Chemistry,* 273 (20), 11991-11994.

Lowry, K. J., Hamson, K. R., Bear, L., Peng, Y. B., Calaluce, R., Evans, M. L., Anglen, J. O. and Allen, W. C. (1997): Polycaprolactone/Glass Bioabsorbable Implant in a Rabbit Humerus Fracture Model. *Journal of Biomedical Materials Research,* 36, 536-541.

Peluso, G., Petillo, O., Mazzarella, L., La Cara, F., Sada, A., Melone, M. A. B., Davies, P. J. A. and Gentle, V. (1996): Cell-Biomaterial Interactions: Role of Transglutaminase Enzyme. *Journal of Materials Science: Materials in Medicine,* 7, 707-711.

Pitt, C. G., Chasalow, F. I., Hibionada, Y. M., Kilmas, D. M. and Schindler, A. (1981): Aliphatic Polyesters. I. The Degradation of Poly(□-Caprolactone) In Vivo. *Journal of Applied Polymer Science,* 26, 3779-3787.

Pitt, C. G. and Gu, Z. (1987): Modification of the Rates of Chain Cleavage of Poly(e-Caprolactone) an Related Polyesters in the Solid State. *Journal of Controlled Release,* 4, 283-292.

Pitt, C. G., Jeffcoat, R., Zweidinger, R. A. and Schindler, A. (1979): Sustained Drug Delivery Systems. I. The Permeability of Poly(□-Caprolactone), Poly(DL-Lactic Acid) and Their Copolymers). *Journal of Biomedical Materials Research,* 13, 479-507.

Rago, R., Mitchen, J. and Wilding, G. (1990): DNA Fluorometric Assay in 96 Well Culture Plates, Using Hoechst 33258 After Cell Lysis by Freezing in Distilled Water. *Biochemistry;* 191, 31-34.

Ruoslahti, E., Hayman, E. G. and Pierschbacher, M. D. (1985): Extracellular Matrices and Cell Adhesion. *Arteriosclerosis,* 5; 6, 581-594. Schamberger, P. C. and Gardella, J. A. (1994): Surface Chemical Modifications of Materials Which Influence Animal Cell Adhesion—A Review. *Colloids and Surfaces B: Biointerfaces,* 2, 209-223.

Quado, B. J. and McDonald, J. A. (1988): Fibronectins Amino-Terminal Matrix Assembly Site is Located Within the 29 Kda Amino Terminal Domain Containing Five Type I Repeats. *Journal of Biological Chemistry,* 263, 19602-19609.

Schwart, M. A., Brown, E. J. and Pazeli, B. (1993): A 50 Kda Integrin Associated Protein is Required for Integrin Regulated Calcium Entry in Endothelial Cells. *Journal of Biological Chemistry,* 268, 19931-19934.

Sinha, R. K., Morris, F., Shah, S. A. and Tuan, R. S. (1994): Surface Composition of Orthopaedic Implant Metals Regulates Cell Attachment, Spreading and Cytoskeletal Organisation of Primary Human Osteoblasts In Vitro. *Clinical Orthopaedics and Related Research;* 305, 258-272.

Smethurst, P. A. and Griffin, M., 1996: Measurement of Tissue Transglutaminase Activity in a Permeabilised Cell System: Its Regulation By Calcium and Nucleotides. *Biochemical Journal,* 313, 803-808.

Smith, K. L., Schimpf, M. E. and Thompson, K. E. (1990): Bioerodible Polymers for Delivery of Macromolecules. *Advanced Drug Delivery Reviews,* 4, 343-357.

Taylor, M. S., Daniels, A. U., Andriano, K. P. and Heller, J. (1994): Six Bioabsorbable Polymers; In Vitro Acute Toxicity of Accumulated Degradation Products. *Journal of Applied Biomaterials,* 5, 151-157.

Ueki, S., Takagi, J. and Saito, Y., (1996): Dual Actions of Transglutaminases in Novel Cell Adhesion. *Journal of Cell Science,* 109, 2727-2735.

Upchurch, H. F., Conway, E., Patterson, J R. and Maxwell, M. D. (1991): Localisation of Cellular Transglutaminase on the Extracellular Matrix after Wounding: Characteristics of the Matrix Bound Enzyme. *Journal of Cellular Physiology,* 149, 375-382.

Verderio, E., Nicholas, B., Gross, S. and Griffin, M. (1998): Regulated Expression of Tissue Transglutaminase In Swiss 3T3 Fibroblasts: Effects on the Processing of Fibronectin, Cell Attachment and Cell Death. *Experimental Cell Research,* 239, 119-138.

Vert, M., Li, S. M., Spenlehauer, G. and Guerin, P. (1992): Bioresorbablility and Biocompatibility of Aliphatic Polyesters. *Journal of Materials Science: Materials in Medicine,* 3, 432-446.

The invention claimed is:

1. A medical implant material comprising a polymer having an external surface, and a complex of a mammalian transglutaminase immobilized on a transglutaminase binding protein immobilized on the polymer surface, wherein the transglutaminase is immobilized in the absence of free divalent metal ions so said transglutaminase is substantially inactive in vitro, and wherein said immobilized transglutaminase promotes biocompatibility of said implant material by enhancing the ability of said implant material to support cell attachment, cell spreading, cell proliferation and cell differentiation.

2. A medical implant material according to claim 1 wherein the transglutaminase is tissue transglutaminase.

3. A medical implant material according to claim 1 wherein the transglutaminase is plasma transglutaminase.

4. A medical implant material according to claim 1 wherein the transglutaminase is prepared from mammalian tissues or cells.

5. A medical implant material according to claim 4 wherein the transglutaminase is prepared from human tissue or cells.

6. A medical implant material according to claim 1 wherein the transglutaminase is a recombinant transglutaminase.

7. A medical implant material according to claim 1 wherein the polymer is a naturally occurring polymer.

8. A medical implant material according to claim 7 wherein the naturally occurring polymer is a naturally occurring extracellular matrix molecule selected from the group consisting of collagen, fibronectin, fibrin, fibrillin, a glycosoaminoglycan and hyaluronic acid.

9. A medical implant material according to claim 1 wherein the polymer is a synthetic polymer.

10. A medical implant material according to claim 9 wherein the synthetic polymer is selected from the group consisting of poly($\epsilon$-caprolactone) (PCL), poly(L-lactide) (PLA), poly(glycolide) (PGA), poly(DL-lactide co-glycolide) (PLG), methacrylates poly(ethylmethacrylate), ethylacrylate, tetrahydro-furfurylmethacrylate, hydroxyethylmethacrylate, silastic, poly(tetra-fluoroethylene), medpore (porous polyethylene), poly(orthoester), poly(dioxane), and co-polymers and blends thereof.

11. A medical implant material according to claim 9 or 10 wherein the polymer is poly-($\epsilon$-caprolactone).

12. A medical implant material according to claim 1 wherein the complex is immobilized on the polymer surface by coating the polymer with the transglutaminase binding protein.

13. A medical implant material according to claim 1 wherein the polymer is porous and wherein the polymer is impregnated with the complex.

14. A medical implant material according to claim 1 wherein the complex is covalently bound to the polymer surface by covalently bonding the transglutaminase binding protein to the polymer surface.

15. A medical implant material according to claim 1 wherein the transglutaminase binding protein is a transglutaminase substrate.

16. A medical implant material according to claim 1 wherein the transglutaminase binding protein is selected from a group consisting of fibronectin, fibrin, fibrinogen, collagen, entactin, osteonectin, osteopontin, thrombospondin, vitronectin, β-lactoglobulin and casein.

17. A medical implant material according to claim 1 wherein the transglutaminase binding protein is fibronectin or a fragment thereof that binds to a transglutaminase.

18. A medical implant material according to claim 17 wherein the fibronectin fragment comprises amino acids 32-608 of the N-terminus of fibronectin, or a fragment thereof.

19. A medical implant material according to claim 1 wherein the transglutaminase binding protein is fibrin or a fragment thereof that binds to a transglutaminase.

20. A medical implant material according to claim 1 wherein the medical implant material further comprises a reinforcing agent.

21. A medical implant material according to claim 20 wherein the reinforcing agent is selected from a group consisting of alumina, alumina-boria-silica, calcium metaphosphate glass fibres, titanium and carbon.

22. A medical implant material according to claim 1 wherein the medical implant material further comprises at least two polymers.

23. A medical implant material according to claim 22 wherein at least one of the polymers is a synthetic polymer.

24. A medical implant material according to claim 22 wherein at least one of the polymers is a natural polymer.

25. A medical implant material according to claim 22 wherein at least one of the polymers is a naturally occurring extracellular matrix molecule selected from the group consisting of collagen, fibronectin, fibrillin, fibrin, a glycosoaminoglycan and hyaluronic acid.

26. A medical implant material according to claim 1 wherein the transglutaminase is provided with a chelating agent.

27. A medical implant material according to claim 26 wherein the chelating agent is EDTA or EGTA.

28. A medical implant material according to claim 26 or 27 wherein the chelating agent is at a concentration of between 5 mM and 0.1 M.

29. A medical implant material according to claim 1, wherein the medical implant material is an artificial tissue, prosthetic device or drug delivery device for implantation into the human or animal body.

30. A medical implant material according to claim 29, wherein the medical implant material is artificial tissue and is selected from the group consisting of artificial bone and artificial teeth.

31. A medical implant material according to claim 29, wherein the medical implant material is a prosthetic device selected from the group consisting of joints, heart valves and blood vessels.

32. A medical implant material according to claim 30, wherein the medical implant material is artificial bone.

33. A medical implant material according to claim 29, wherein the medical implant material is biodegradable.

34. A medical implant material according to claim 30, wherein the medical implant material is artificial teeth.

35. A medical implant material according to claim 6, wherein the recombinant transglutaminase is purified.

36. A medical implant material according to claim 1, wherein the transglutaminase is tissue transglutaminase and the transglutaminase binding protein is fibronectin.

37. A medical implant material according to claim 1, wherein the transglutaminase is plasma transglutaminase and the transglutaminase binding protein is fibronectin.

* * * * *